(12) United States Patent
Shahaf et al.

(10) Patent No.: US 10,099,019 B2
(45) Date of Patent: *Oct. 16, 2018

(54) NASAL DELIVERY DEVICE

(71) Applicant: SIPNOSE LTD., Yokne'Am Ilit (IL)

(72) Inventors: Daniel Shahaf, M.P. Emek Ha-Yarden (IL); Joseph Hadash, Lapid (IL)

(73) Assignee: SIPNOSE LTD., Yokne'am Ilit (IL)

( * ) Notice: Subject to any disclaimer, the term of this patent is extended or adjusted under 35 U.S.C. 154(b) by 10 days.

This patent is subject to a terminal disclaimer.

(21) Appl. No.: 15/414,639

(22) Filed: Jan. 25, 2017

(65) Prior Publication Data

US 2017/0128678 A1 May 11, 2017

Related U.S. Application Data

(60) Continuation-in-part of application No. 14/977,679, filed on Dec. 22, 2015, which is a division of
(Continued)

(51) Int. Cl.
*A61M 15/00* (2006.01)
*A61M 11/02* (2006.01)
(Continued)

(52) U.S. Cl.
CPC .......... *A61M 11/02* (2013.01); *A61K 9/0043* (2013.01); *A61K 39/00* (2013.01); *A61M 11/00* (2013.01);
(Continued)

(58) Field of Classification Search
CPC ............ A61B 5/00; A61M 2210/0618; A61M 2210/0625; A61M 15/0013;
(Continued)

(56) References Cited

U.S. PATENT DOCUMENTS 6,050,444 A    4/2000  Sugg
6,526,966 B1 * 3/2003  Peesay ............... A61J 9/00
                                                 128/200.14
(Continued)

FOREIGN PATENT DOCUMENTS

WO    2012/029064 A1    3/2012

OTHER PUBLICATIONS

International Search Report of PCT/IL2011/000702, dated Jan. 17, 2012.
(Continued)

*Primary Examiner* — Kari Rodriquez
*Assistant Examiner* — Victoria Murphy

(57) ABSTRACT

The present invention provides a method for delivering a substance to the nasal cavity of a subject in which drawing air from a mouthpiece triggers release of a substance to a subject's nasal cavities. The device comprises a container for containing the substance in fluid communication with a nosepiece, a valve with an active configuration and an inactive configuration, and a trigger mechanism to reconfigure the valve from its inactive configuration to its active configuration and vice versa. Drawing air from the mouthpiece, e.g., when the subject takes in air by mouth, activates the trigger mechanism, thereby reconfiguring the valve from its inactive configuration to its active configuration for a predetermined period of time and delivering the substance from the device to a nasal cavity of the subject.

39 Claims, 22 Drawing Sheets

Related U.S. Application Data application No. 13/783,620, filed on Mar. 4, 2013, now Pat. No. 9,339,617, which is a continuation-in-part of application No. PCT/IL2011/000702, filed on Sep. 1, 2011.

(60) Provisional application No. 61/427,181, filed on Dec. 26, 2010, provisional application No. 61/379,394, filed on Sep. 2, 2010.

(51) Int. Cl.
  *A61M 11/00* (2006.01)
  *A61M 15/08* (2006.01)
  *A61M 16/20* (2006.01)
  *A61K 9/00* (2006.01)
  *A61K 39/00* (2006.01)
  *A61M 16/00* (2006.01)

(52) U.S. Cl.
  CPC .......... *A61M 11/006* (2014.02); *A61M 15/00* (2013.01); *A61M 15/003* (2014.02); *A61M 15/009* (2013.01); *A61M 15/0016* (2014.02); *A61M 15/0025* (2014.02); *A61M 15/0091* (2013.01); *A61M 15/0093* (2014.02); *A61M 15/0098* (2014.02); *A61M 15/08* (2013.01); *A61M 16/20* (2013.01); *A61M 16/207* (2014.02); *A61K 2039/543* (2013.01); *A61M 2016/0015* (2013.01); *A61M 2202/064* (2013.01); *A61M 2202/30* (2013.01); *A61M 2210/0618* (2013.01); *A61M 2210/0625* (2013.01)

(58) Field of Classification Search
  CPC .......... A61M 15/0091; A61M 15/0045; A61M 15/009; A61M 15/08; A61M 2016/0027

USPC ............. 128/200.11, 200.15, 200.26, 207.18
  See application file for complete search history.

(56) References Cited

U.S. PATENT DOCUMENTS

| | | |
|---|---|---|
| 6,543,445 B1 | 4/2003 | Hopper |
| 6,715,485 B1 | 4/2004 | Djupesland |
| 7,784,460 B2 | 8/2010 | Djupesland et al. |
| 7,975,690 B2 | 7/2011 | Djupesland |
| 8,800,555 B2 | 8/2014 | Djupesland |
| 2002/0183690 A1* | 12/2002 | Arnisolle ............ A61M 5/2066 604/83 |
| 2004/0112378 A1* | 6/2004 | Djupesland ............ A61B 5/085 128/203.12 |
| 2005/0121023 A1 | 6/2005 | Braithwaite |
| 2005/0268909 A1 | 12/2005 | Bonney et al. |
| 2006/0110471 A1 | 5/2006 | Nichols |
| 2007/0125371 A1 | 6/2007 | Djupesland |
| 2007/0158352 A1 | 7/2007 | Cheng |
| 2009/0205658 A1 | 8/2009 | Tanaka et al. |

OTHER PUBLICATIONS

Written Opinion of the International Search Authority of PCT/IL2011/000702, dated Jan. 17, 2012.
International Preliminary Report on Patentability Chapter I, of PCT/IL2011/000702, dated Mar. 5, 2013.
Smith J., "Coordination of Eating, Drinking and Breathing in Adults", Chest Journal, American College of Chest Physicians, pp. 578-582, vol. 96, No. 33 (1989).

* cited by examiner

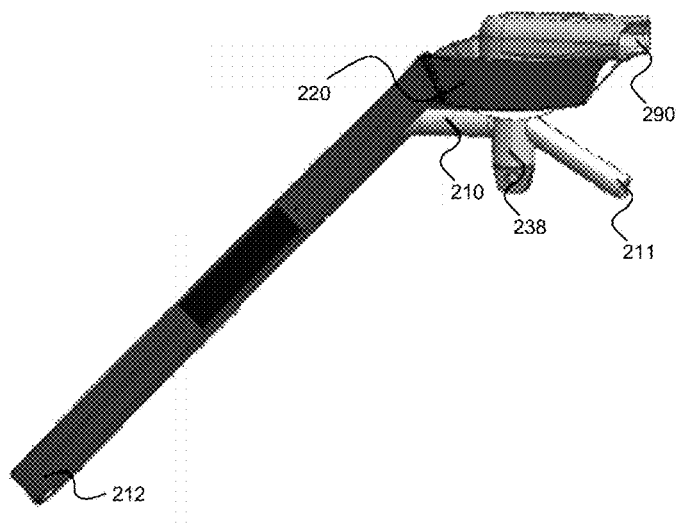
Fig. 8
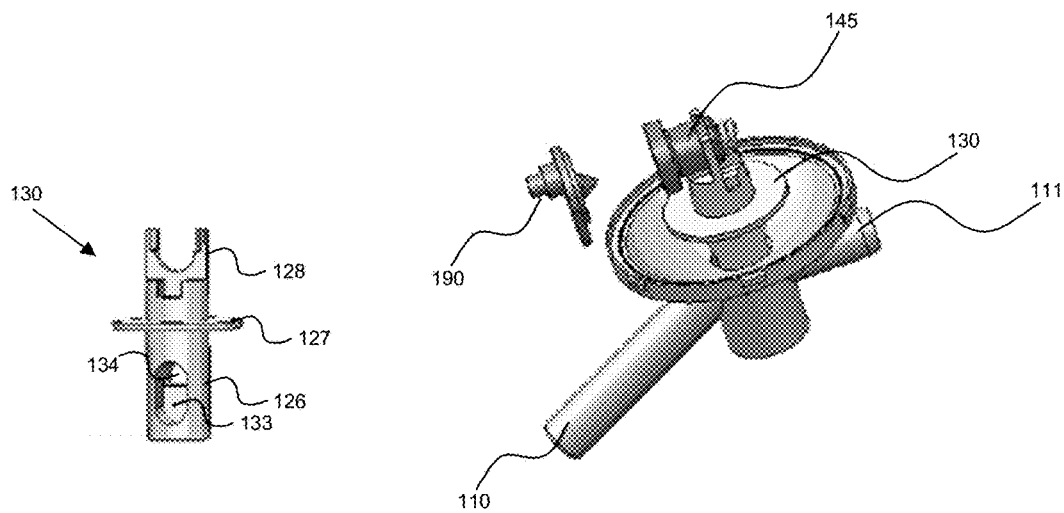
Fig. 9
Fig. 10

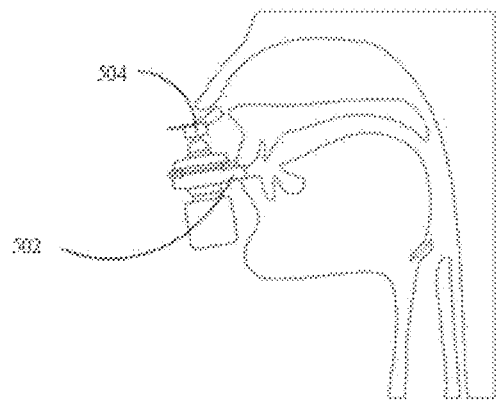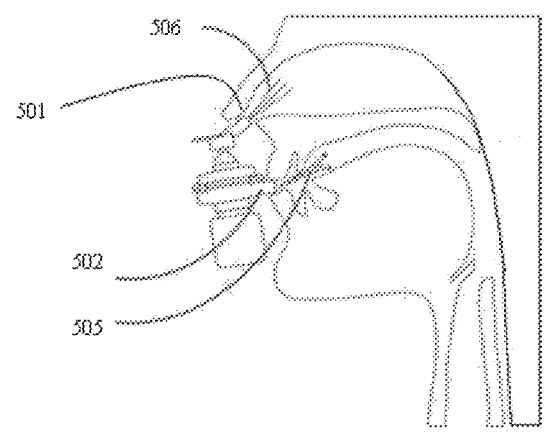
Fig. 13          Fig. 14
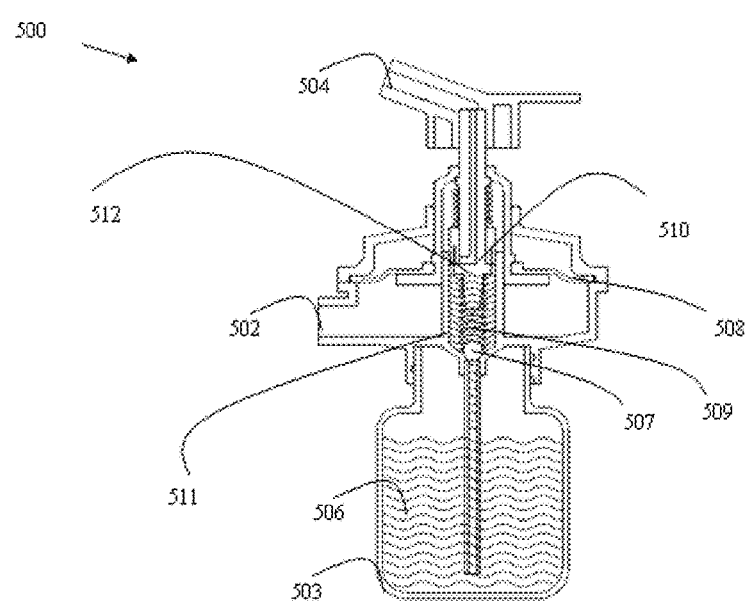
Fig. 15

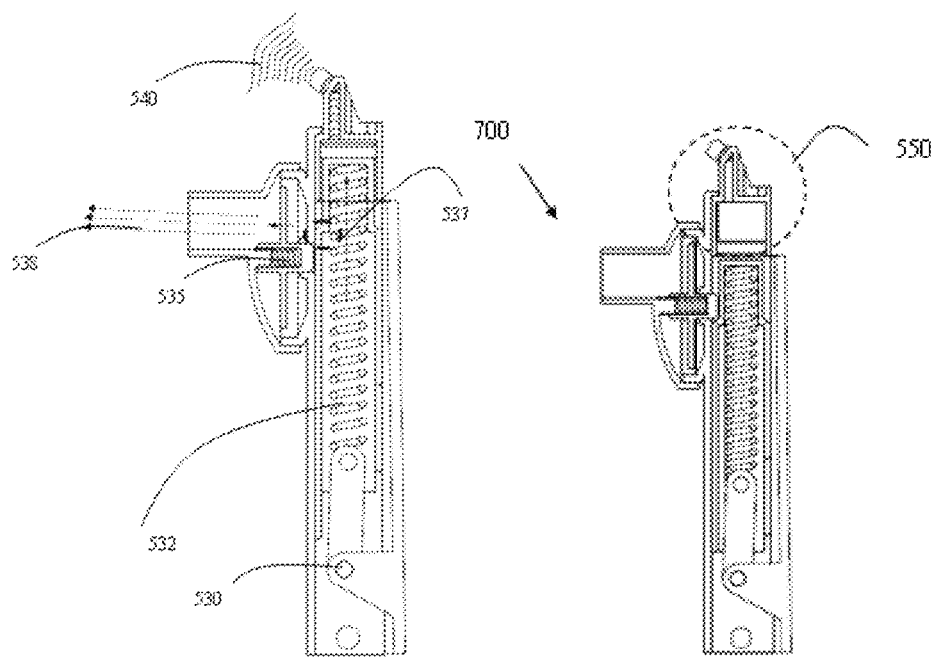
Fig. 35          Fig. 36
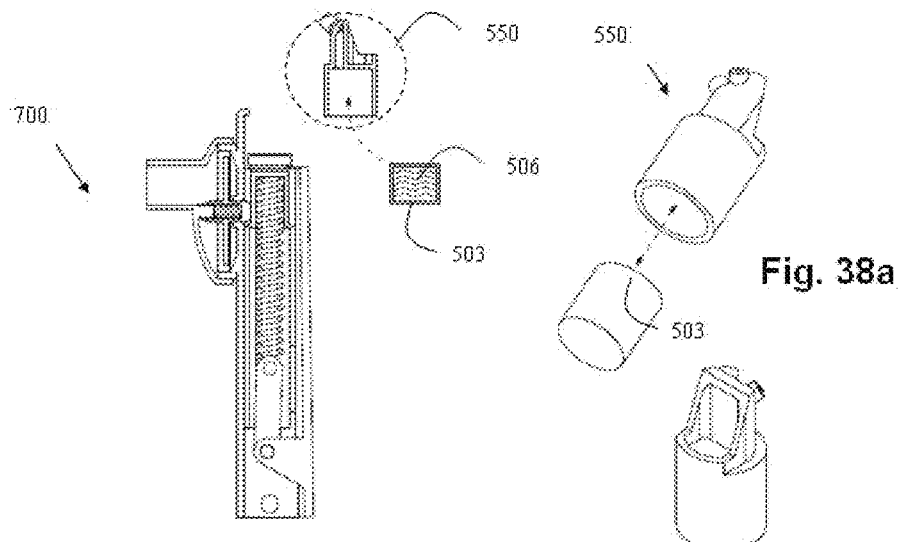
Fig. 37          Fig. 38b
Fig. 38a

NASAL DELIVERY DEVICE

CROSS REFERENCE TO RELATED APPLICATIONS

This application is a Continuation-in-Part of U.S. application Ser. No. 14/977,679, filed 22 Dec. 2015, which is a Divisional of U.S. application Ser. No. 13/783,620, filed 4 Mar. 2013, which is a Continuation-in-Part of PCT International Application Number PCT/IL2011/000702, filed 1 Sep. 2011, which claims priority from U.S. Provisional application No. 61/427,181, filed 26 Dec. 2010, and U.S. Provisional application No. 61/379,394, filed 2 Sep. 2010. All of these applications are hereby incorporated by reference in their entirety.

FIELD OF THE INVENTION

The present invention generally relates to a nasal substance delivery device, and more specifically, to a drinking/breathing-actuated device for delivering a substance to a nasal cavity of a subject in a variety of different delivery methods.

BACKGROUND OF THE INVENTION

Nasal delivery of a substance (e.g., a drug, a vaccine, etc.) can be useful both for treating diseases or disorders of the nasal passageways themselves and for treating other disorders or conditions through the systemic route (e.g., vaccine, neurological, etc.). The advantages of nasal delivery of a substance are, among others, the following:

(a) a rich vascular plexus—a direct route into the blood stream; (b) avoiding gastrointestinal destruction as drug degradation which is observed in the gastrointestinal tract is absent. (c) Hepatic first pass metabolism (destruction of drugs by liver enzymes) is absent; (d) rates of absorption and plasma concentrations are comparable to intravenous administration; (e) ease, convenience and safety; (f) rapidly achievement of therapeutic brain and spinal cord (CNS) drug concentrations; (g) rapid drug absorption and quick onset of action can be achieved; (h) the bioavailability of larger drug molecules can be improved by means of absorption enhancers or other approaches; (i) The nasal bioavailability for smaller drug molecules is good; (j) drugs that are orally not absorbed can be delivered to the systemic circulation by nasal drug delivery; (k) based on published information, the nasal route was indicated as an alternate to parenteral route, especially for protein and peptide drugs; (l) convenient for the patient, especially for those on long term therapy, when compared with parenteral medication.

On the other hand, the limitations of nasal delivery of a substance are:

(a) the histological toxicity of absorption enhancers used in nasal drug delivery system is not yet clearly established; (b) relatively inconvenient to patients when compared to oral delivery systems since there is a possibility of nasal irritation; (c) nasal cavity provides smaller absorption surface area when compared to (Gastro intestinal tract GIT).

Therapy through intranasal administration has been an accepted form of treatment in many countries. In recent years many drugs have been shown to achieve better systemic bioavailability through nasal route than by oral administration. Advances in biotechnology have made available a large number of protein and peptide drugs for the treatment of a variety of diseases. These drugs are unsuitable for oral administration because they are significantly degraded in the gastrointestinal tract or considerably metabolized by first pass effect in the liver. Also, the parenteral route is inconvenient for long term therapy. Of many alternate routes tried, intranasal drug delivery is found much promising for administration of such drugs.

There are many traditional devices that are adapted to supply substances to the nasal cavity. These devices include, for example, syringed nose drops, pump spray devices, and fluorinated propellant metered dose inhalers (MDI). These traditional devices have not generally been able to achieve the particle sizes necessary to maximize efficacy while helping mitigate undesired pulmonary absorption. For example, both eye dropper type devices and simple spray devices typically present medicament into the nasal cavity in a stream. The result is that much of the medicament simply runs out of the patient's nose, and only a small amount of the drug is absorbed, with even less of the drug reaching the nasal epithelia.

In the recent years a few companies have developed novel drug delivery devices which are activated when a subject exhales air from the lungs through the mouth. As a result of the air exhale, the soft palate is closed, and thereby operates to isolate the nasal passageways from the remainder of the pulmonary system. By that, the soft palate acts as a natural check valve preventing the flow of air between the lungs and the nasal cavity. Thus, in these air-exhale based devices, it is believed that nasal substance delivery can be improved if the patient is exhaling orally while the substance is being sprayed into the nasal passages. One nasal delivery device that takes advantage of this phenomenon is shown in U.S. Pat. No. 6,715,485 to Optinose. This patent application discloses a delivery device for delivering a substance to the nasal airway of a subject, in particular the posterior region of the nasal airway, the delivery device comprising: a closure unit for causing the closure of the oropharyngeal velum of the subject, and a delivery unit for delivering a gas flow entraining a substance to one of the nostrils of the subject at such a driving pressure as to flow around the posterior margin of the nasal septum and out of the other nostril of the subject, wherein the delivery unit comprises a nosepiece which includes an outlet through which the gas flow in use is delivered to the one nostril and a sealing member for sealing the one nostril to the outlet such as in use to prevent the escape of the gas flow through the one nostril.

The present invention takes advantage of the normal swallowing mechanism in which the soft palate closes, in the delivery process of a substance to nose. In this mechanism the isolation of the nose passageways from the respiratory system is better than in the case of air exhalation (on which the nasal drug delivery devices known in the prior art is based). Furthermore, the present invention is able to deliver a desired amount of substance to the nasal epithelium while preventing entry into the pulmonary tract and the lungs. This substance delivery device has to comply with the following key requirements: a. they have to be accurate in the doses of the substance they provide, b. good penetration to the nasal canals, c. painless, d. with minimal stomach deposition, e. with minimal lung deposition, f. easy to use, g. with improved patient compliance, h. washing of the drug flavor, i. suitable platform for various drugs and vaccines, j. and with subject-independent actuation. The present invention is intended to comply with all these requirements.

SUMMARY OF THE INVENTION

It is one object of the present invention to provide an air-intake actuated device adapted for delivering a substance to a nasal cavity of a subject, said device comprising:

a. a container for containing said substance;
b. a nosepiece extending from said device for placement in proximity to a nose of said subject, said nosepiece being in fluid communication with said container;
c. a valve mechanically connectable to said container, characterized by at least two configurations: (i) an active configuration in which said valve enables delivery of predetermined amount of said substance from said container to said nasal cavity via said nosepiece; and, (ii) an inactive configuration, in which said valve prevents delivery of said predetermined amount of said substance from said container to said nasal cavity;
d. a mouthpiece extending from said device for placement in a mouth of said subject; and,
e. a trigger mechanism adapted to reconfigure said valve from said active configuration to said inactive configuration, and vice versa;

wherein said trigger mechanism is activated by means of said subject intaking air through said mouthpiece; further wherein said trigger mechanism is adapted to reconfigure said valve from said inactive configuration to said active configuration for a predetermined period of time in response to said subject intake of air.

It is another object of the present invention to provide the air-intake actuated device as defined above, wherein said trigger mechanism is adapted to reconfigure said valve from said active configuration to said inactive configuration when said subject ceases said intake.

It is another object of the present invention to provide the air-intake actuated device as defined above, wherein said trigger mechanism comprises a flexible membrane; said membrane is in mechanical communication with said valve; such that when said subject intake air, said membrane is relocated from its initial position and said valve is opened.

It is another object of the present invention to provide the air-intake actuated device as defined above, additionally comprising an intermediate compartment adapted to be filled with predetermined amount of said substance; such that said delivery of said substance to said subject is from said intermediate compartment.

It is another object of the present invention to provide the air-intake actuated device as defined above, wherein the operation of said trigger mechanism is synchronized with said intake of air by said subject.

It is another object of the present invention to provide the air-intake actuated device as defined above, wherein said trigger mechanism comprises a pulsation mechanism adapted to reconfigure said valve from said inactive configuration to said active configuration and vice versa in sequence of pulses, each of which is characterized by a predetermined length of pulse, said valve adapted to a release said predetermined amount of said substance according to said sequence of pulses.

It is another object of the present invention to provide the air-intake actuated device as defined above, wherein in each said pulse at least two doses of said predetermined amount of said substance are released.

It is another object of the present invention to provide the air-intake actuated device as defined above, wherein said nosepiece is in fluid communication with said valve by means of a spray nozzle.

It is another object of the present invention to provide the air-intake actuated device as defined above, wherein said spray nozzle is characterized by a diameter which influences on said predetermined period of time.

It is another object of the present invention to provide the air-intake actuated device as defined above, further comprising a cap adapted to cover at least a portion of the components of said device for sterilization/aseptic purposes.

It is another object of the present invention to provide the air-intake actuated device as defined above, wherein said cap comprises an opening.

It is another object of the present invention to provide the air-intake actuated device as defined above, wherein said container adapted to be connected to an external container, said external container adapted to fill said container with said substance.

It is another object of the present invention to provide the air-intake actuated device as defined above, wherein said external container adapted to fill said container with a predetermined dose of said substance.

It is another object of the present invention to provide the air-intake actuated device as defined above, further comprising indicating means adapted to indicate the amount of said substance within said container.

It is another object of the present invention to provide the air-intake actuated device as defined above, wherein said indicating means is a transparent window located on a side of said container.

It is another object of the present invention to provide the air-intake actuated device as defined above, wherein said substance is a drug selected from a group consisting of: Anti-Angiogenesis agents, Antisense, anti-ulcer, butorphanol, Calcitonin and analogs, Cyclooxygenase (COX-II) inhibitors, desmopressin and analogs, dihydroergotamine, Dopamine agonists and antagonists, Enkephalins and other opioid peptides, Growth hormone and analogs, growth hormone releasing hormone, Growth hormone antagonists, Immunoglobulin E (IgE) suppressors, Insulin, insulinotropin and analogs, Ketamine, Kytril (granisetron), Leutenizing hormone releasing hormone and analogs, lidocaine, metoclopramide, Midazolam, Narcotic analgesics, neuraminidase inhibitors, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, vasopressin, or any combination thereof.

It is another object of the present invention to provide the air-intake actuated device as defined above, wherein said substance is a vaccine with or without carriers and/or adjuvant selected from the group consisting of: Prophylactics and therapeutic antigens, subunit protein, peptide and polysaccharide, polysaccharide conjugates, toxoids, genetic based vaccines, live attenuated reassortant, inactivated whole cells, viral and bacterial vectors for the treatment of arthritis, *Lactobacillus* species: *Lactobacillus acetotolerans, Lactobacillus acidifarinae, Lactobacillus acidipiscis, Lactobacillus acidophilus* (*Doderlein bacillus*), *Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustorum, Lactobacillus curvatus, Lactobacillus delbrueckii, Lactobacillus delbrueckii* subsp. *Bulgaricus, Lactobacillus delbrueckii* subsp. *Lactis, Lactobacillus diolivorans, Lactobacillus equi, Lactobacillus equigenerosi, Lactobacillus farraginis, Lactobacillus farciminis, Lactoba-* cillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus hammesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefiranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae, Lactobacillus zymae, Probiotics selected from a group consisting of Lactic acid bacteria (LAB) and bifidobacteria, or any combination thereof; said substance is used for the treatment of at least one selected from a group consisting of cholera, moraxella catarrhali, cocaine addiction, Haemophilus influenzae type b (Hib), meningococcus, measles, mumps, rubella, varicella, yellow fever, Respiratory syncytial virus, pneumococcus, streptococcus, typhoid, influenza, hepatitis, including hepatitis A, B, C and F, polio, human immunodeficiency virus (HIV), parainfluenza, rotavirus, cytomegalovirus (CMV), chlamydia, non-typeable haemophilus, moraxella catarrhalis, human papilloma virus, tuberculosis including Bacillus Calmette-Guerin (BCG), gonorrhoea, asthma, atheroschlerosis, malaria, otitis media, E-coli, Alzheimer's disease, H. Pylori, salmonella, diabetes, cancer, herpes simplex, Staphylococcus aureus, Streptoccocus, or any combination thereof.

It is another object of the present invention to provide the air-intake actuated device as defined above, wherein said substance is used for the treatment of at least one selected from a group consisting of cholera, moraxella catarrhali, cocaine addiction, Hib, meningococcus, measles, mumps, rubella, varicella, yellow fever, Respiratory syncytial virus, pneumococcus, streptococcus, typhoid, influenza, hepatitis, including hepatitis A, B, C and F, polio, HIV, parainfluenza, rotavirus, CMV, chlamydia, non-typeable haemophilus, moraxella catarrhalis, human papilloma virus, tuberculosis including BCG, gonorrhoea, asthma, atherosclerosis, malaria, otitis media, E-coli, Alzheimer's disease, H. Pylori, salmonella, diabetes, cancer, herpes simplex, Staphylococcus aureus, Streptoccocus, or any combination thereof.

It is another object of the present invention to provide the air-intake actuated device as defined above, wherein the substance is a peptide or protein therapeutic agent such as cytokines, hormones, clotting factors, vaccines, monoclonal antibody.

It is another object of the present invention to provide the air-intake actuated device as defined above, used for the treatment of central nervous system (CNS) disorders, brain disorders such as: brain cancer, acute brain injury, spinal cord injury, Alzheimer's disease, Neurogenesis, Parkinson's disease, depression, Epilepsy, schizophrenia by the delivery of substances such as: Neurotrophins, brain-derived neurotrophic factor (BDNF), glial cell-derived neurotrophic factor (GDNF), anti-epidermal growth factor receptor antibodies (anti EGF receptor AB), Enzymes such as Lysosomal enzyme, Neuregulin.

It is another object of the present invention to provide the air-intake actuated device as defined above, wherein said substance is a therapeutic substance selected from a group consisting of: agents for the common cold, Anti-addiction, anti-infectives, analgesics, anesthetics, anorexics, antiarthritics, anti-allergy agents, antiasthmatic agents, anticonvulsants, anti-depressants, antidiabetic agents, anti-depressants, anti-diuretics, anti-emetics, antihistamines, anti-inflammatory agents, antimigraine preparations, antimotion sickness preparations, antinauseants, antineoplastics, anti-obesity, antiosteoporeteic, antiparkinsonism drugs, antipruritics, antipsychotics, antipyretics, anticholinergics, benzodiazepine antagonists, bone stimulating agents, central nervous system stimulants, hormones, hypnotics, immunosuppressives, prostaglandins, proteins, peptides, polypeptides and other macromolecules, psychostimulants, rhinitis treatment, sedatives, sexual hypofunction, tranquilizers and vitamins including B12, probiotics, natural oils, natural ingredients, or any combination thereof.

It is another object of the present invention to provide the air-intake actuated device as defined above, wherein said substance may be delivered to said nasal cavity in a form selected from the group consisting of: a powder; a granule; a cachet; a capsule; a tablet; a paste; a cream; a gel; an ointment; a salve; a foam; a paste; a lotion; a cream; an oil suspension; a spray; a suspension; a solution; an emulsion; a patch; a stick; a spray, preferably a nasal spray, or a buccal spray; a mouth wash, an aerosol, from a Venturi effect, and a drink.

It is another object of the present invention to provide the air-intake actuated device as defined above, wherein said substance is selected from a group consisting of natural oils; Mint oils, Peppermint oil, Spearmint oil, Menthol, Olive oil, Eucalyptus oil, Amino acids, fatty acids and any combination thereof.

It is another object of the present invention to a method for delivering a substance to a nasal cavity of a subject, said method comprising steps of:

a. providing an air-intake actuated device adapted for delivering a substance to a nasal cavity of a subject, said device comprising: (i) a container for containing said substance; (ii) a nosepiece extending from said device for placement in proximity to a nose of said subject, said nosepiece being in fluid communication with said container; (iii) a valve mechanically connectable to said container, characterized by at least two configurations: (i) an active configuration in which said valve enables delivery of predetermined amount of said substance from said container to said nasal cavity via said nosepiece; and, (ii) an inactive configuration, in which said valve prevents delivery of said predetermined amount of said substance from said container to said nasal cavity; (iv) a mouthpiece extending from said device for placement in a mouth of said subject; and, a (v) trigger mechanism adapted to reconfigure said valve from said active configuration to said inactive configuration, and vice versa; wherein said trigger mechanism is activated by means of said subject intaking air through said mouthpiece; further wherein said trigger mechanism is adapted to reconfigure said valve from said inactive configuration to said active configuration for a predetermined period of time in response to said subject intake of air;

b. placing said nosepiece in or around the nose of said subject;

c. placing said mouthpiece in the mouth of said subject;

d. inhaling air; thereby reconfiguring said valve from said inactive configuration to said active configuration for a predetermined period of time in response;

e. releasing a predetermined amount of said substance from said container to said nosepiece.

It is another object of the present invention to provide the method as defined above, further comprising step of reconfiguring said valve via said trigger mechanism from said active configuration to said inactive configuration when said subject ceases said intake.

It is another object of the present invention to provide the method as defined above, additionally comprising step of providing said trigger mechanism with a flexible membrane; said membrane is in mechanical communication with said valve; such that when said subject intake air, said membrane is relocated from its initial position and said valve is opened.

It is another object of the present invention to provide the method as defined above, additionally comprising step of providing said device with an intermediate compartment adapted to be filled with predetermined amount of said substance; such that said delivery of said substance to said subject is from said intermediate compartment.

It is another object of the present invention to provide the method as defined above, further comprising step of synchronizing the operation of said trigger mechanism with said intake of air by said subject.

It is another object of the present invention to provide the method as defined above, further comprising step of providing said trigger mechanism with a pulsation mechanism adapted to reconfigure said valve from said inactive configuration to said active configuration and vice versa in sequence of pulses, each of which is characterized by a predetermined length of pulse, said valve adapted to a release said predetermined amount of said substance according to said sequence of pulses.

It is another object of the present invention to provide the method as defined above, further comprising step of releasing in each said pulse at least two doses of said predetermined amount of said substance.

It is another object of the present invention to provide the method as defined above, wherein said nosepiece is in fluid communication with said valve by means of a spray nozzle.

It is another object of the present invention to provide the method as defined above, wherein said spray nozzle is characterized by a diameter which influences on said predetermined period of time.

It is another object of the present invention to provide the method as defined above, further comprising step of providing said device with a cap adapted to cover at least a portion of the components of said device for sterilization/aseptic purposes.

It is another object of the present invention to provide the method as defined above, wherein said cap comprises an opening.

It is another object of the present invention to provide the method as defined above, wherein said container adapted to be connected to an external container, said external container adapted to fill said container with said substance.

It is another object of the present invention to provide the method as defined above, further comprising step of filling said container by said external container with a predetermined dose of said substance.

It is another object of the present invention to provide the method as defined above, further comprising step of providing said container with indicating means adapted to indicate the amount of said substance within said container.

It is another object of the present invention to provide the method as defined above, wherein said indicating means is a transparent window located on a side of said container.

It is another object of the present invention to provide the method as defined above, wherein said substance is a drug selected from a group consisting of: Anti-Angiogenesis agents, Antisense, anti-ulcer, butorphanol, Calcitonin and analogs, COX-II inhibitors, desmopressin and analogs, dihydroergotamine, Dopamine agonists and antagonists, Enkephalins and other opioid peptides, Growth hormone and analogs, growth hormone releasing hormone, Growth hormone antagonists, IgE suppressors, Insulin, insulinotropin and analogs, Ketamine, Kytril (granisetron), Leutenizing hormone releasing hormone and analogs, lidocaine, metoclopramide, Midazolam, Narcotic analgesics, neuraminidase inhibitors, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, vasopressin, or any combination thereof.

It is another object of the present invention to provide the method as defined above, additionally comprising step of selecting said substance from a vaccine with or without carriers and/or adjuvant selected from the group consisting of: Prophylactics and therapeutic antigens, subunit protein, peptide and polysaccharide, polysaccharide conjugates, toxoids, genetic based vaccines, live attenuated reassortant, inactivated whole cells, viral and bacterial vectors for the treatment of arthritis, *Lactobacillus* species: *Lactobacillus acetotolerans, Lactobacillus acidifarinae, Lactobacillus acidipiscis, Lactobacillus acidophilus* (*Doderlein bacillus*), *Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustorum, Lactobacillus curvatus, Lactobacillus delbrueckii, Lactobacillus delbrueckii* subsp. *Bulgaricus, Lactobacillus delbrueckii* subsp. *Lactis, Lactobacillus diolivorans, Lactobacillus equi, Lactobacillus equigenerosi, Lactobacillus farraginis, Lactobacillus farciminis, Lactobacillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus ham-*

*mesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefiranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae, Lactobacillus zymae,* Probiotics selected from a group consisting of Lactic acid bacteria (LAB) and bifidobacteria, or any combination thereof; said substance is used for the treatment of at least one selected from a group consisting of cholera, *moraxella catarrhali*, cocaine addiction, Hib, meningococcus, measles, mumps, rubella, varicella, yellow fever, Respiratory syncytial virus, pneumococcus, *streptococcus*, typhoid, influenza, hepatitis, including hepatitis A, B, C and F, polio, HIV, parainfluenza, rotavirus, CMV, *chlamydia*, non-typeable *haemophilus, moraxella catarrhalis*, human papilloma virus, tuberculosis including BCG, gonorrhoea, asthma, atherosclerosis, malaria, otitis media, *E-coli,* Alzheimer's disease, *H. Pylori, salmonella*, diabetes, cancer, herpes simplex, *Staphylococcus aureus, Streptoccocus,* or any combination thereof.

It is another object of the present invention to provide the method as defined above, wherein said substance is used for the treatment of at least one selected from a group consisting of cholera, *moraxella catarrhali*, cocaine addiction, Hib, meningococcus, measles, mumps, rubella, varicella, yellow fever, Respiratory syncytial virus, pneumococcus, *streptococcus*, typhoid, influenza, hepatitis, including hepatitis A, B, C and F, polio, HIV, parainfluenza, rotavirus, CMV, *chlamydia*, non-typeable *haemophilus, moraxella catarrhalis*, human papilloma virus, tuberculosis including BCG, gonorrhoea, asthma, atherosclerosis, malaria, otitis media, *E-coli,* Alzheimer's disease, *H. Pylori, salmonella*, diabetes, cancer, herpes simplex, *Staphylococcus aureus, Streptoccocus,* or any combination thereof.

It is another object of the present invention to provide the method as defined above, wherein the substance is a peptide or protein therapeutic agent such as cytokines, hormones, clotting factors, vaccines, monoclonal antibody.

It is another object of the present invention to provide the method as defined above, used for the treatment of CNS disorders, brain disorders such as: brain cancer, acute brain injury, spinal cord injury, Alzheimer's disease, Neurogenesis, Parkinson's disease, depression, Epilepsy, schizophrenia by the delivery of substances such as: Neurotrophins, BDNF, GDNF, anti EGF receptor AB, Enzymes such as Lysosomal enzyme, Neuregulin.

It is another object of the present invention to provide the method as defined above, wherein said substance is a therapeutic substance selected from a group consisting of: Agents for the common cold, Anti-addiction, anti-infectives, analgesics, anesthetics, anorexics, antiarthritics, anti-allergy agents, antiasthmatic agents, anticonvulsants, anti-depressants, antidiabetic agents, anti-depressants, anti-diuretics, anti-emetics, antihistamines, anti-inflammatory agents, antimigraine preparations, antimotion sickness preparations, antinauseants, antineoplastics, anti-obesity, antiosteoporeteic, antiparkinsonism drugs, antipruritics, antipsychotics, antipyretics, anticholinergics, benzodiazepine antagonists, bone stimulating agents, central nervous system stimulants, hormones, hypnotics, immunosuppressives, prostaglandins, proteins, peptides, polypeptides and other macromolecules, psychostimulants, rhinitis treatment, sedatives, sexual hypofunction, tranquilizers and vitamins including B12, probiotics, natural oils, natural ingredients, or any combination thereof.

It is another object of the present invention to provide the method as defined above, wherein said substance is delivered to said nasal cavity in a form selected from the group consisting of: a powder, a granule; a cachet; a capsule; a tablet; a paste; a cream; a gel; an ointment; a salve; a foam; a paste; a lotion; a cream; an oil suspension; a spray; a suspension; a solution; an emulsion; a patch; a stick; a spray, preferably a nasal spray, or a buccal spray; a mouth wash; an aerosol, from a Venturi effect; and a drink.

It is another object of the present invention to provide the method as defined above, additionally comprising step of selecting said substance from a group consisting of natural oils; Mint oils, Peppermint oil, Spearmint oil, Menthol, Olive oil, *Eucalyptus* oil, Amino acids, fatty acids and any combination thereof.

BRIEF DESCRIPTION OF THE FIGURES

For a better understanding of the invention and to show how the same may be carried into effect, reference will now be made, purely by way of example, to the accompanying drawings in which like numerals designate corresponding elements or sections throughout. In the accompanying drawings:

FIG. 8 is a schematic side-view illustration of the drinking-actuated substance delivery device according to another embodiment of the present invention;

FIG. 9 is a schematic illustration of the controlling member according to one embodiment of the present invention;

FIG. 10 is a schematic illustration of the specific elements of the drinking-actuated substance delivery device according to another embodiment of the present invention;

FIGS. 13-14 illustrate the basic concept behind the idea.

FIGS. 15-19b illustrate a first specific mechanism of the inhaling-actuating device 500.

FIGS. 18a-18b and 19a-19b provide a closer view of the actuation step of device 500.

FIGS. 29-38 illustrate a third mechanism 700 based on the intake of air.

FIGS. 38a-38b illustrate the top part 550 prior to and post loading of the medicament 560.

Figure 1:
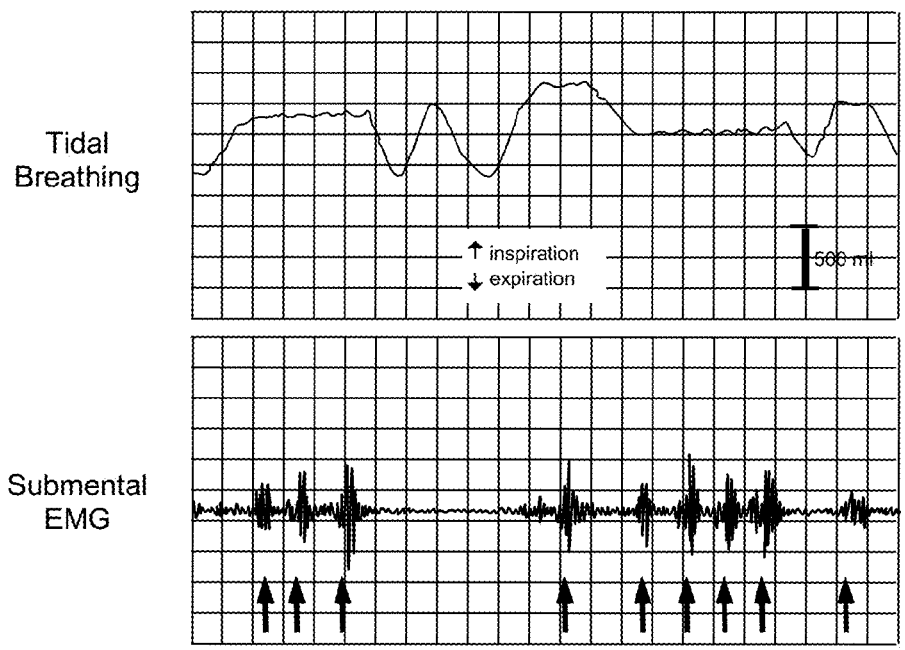
FIG. 1 is an illustration of the pattern of breathing while drinking according to a study of J. Smith et al.

The drawings together with the description make apparent to those skilled in the art how the invention may be embodied in practice.

DETAILED DESCRIPTION OF THE PREFERRED EMBODIMENTS

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting. The present invention discloses an intranasal substance delivery platform, giving synchronized delivery of drug and improving patient's compliance by eliminating bad flavor and insuring dose delivery.

The term 'substance' refers hereinafter to any material which may be used for delivery to the nasal cavity of a subject for medical and alike purposed. According to different embodiments of the present invention, the substance may be delivered to the nasal cavity in a form of a powder; a granule; a cachet; a capsule; a tablet; a paste; a cream; a gel; an ointment; a salve; a foam; a paste; a lotion; a cream; an oil suspension; a spray; a suspension; a solution; an emulsion; a patch; a stick; a spray; preferably a nasal spray, or a buccal spray; a mouth wash; an aerosol from a Venturi effect; or a drink.

The term 'pressure gradient' refers hereinafter to physical quantity that describes in which direction and/or at what rate the pressure changes the most rapidly around a particular location.

The term 'suction' refers hereinafter to the flow of a fluid (e.g., air, liquid) into a partial vacuum, or region of low pressure. The pressure gradient between this region and the ambient pressure will propel matter toward the low pressure area.

The term 'drinking' in the current invention is associated with the physiological process of swallowing in the human or animal body that makes something pass from the mouth, to the pharynx, into the esophagus, with the shutting of the epiglottis and closing the soft palate. According to the present invention, drinking is accompanied with suction of a fluid through a tubule.

The term 'nasal passageways' refers hereinafter to the nasal passageways of a nose of a subject.

The term 'release' refers hereinafter to extraction of substance in a manner which can be, for example, spraying, sprinkling, scattering, dispersing, etc.

The term 'predetermined amount of substance' is a specific dose of a substance that can be regulated by the device.

The term 'coordination' refers hereinafter to a synchronized order of the following: mastication, deglutition and respiration in which an aspiration is prevented.

According to the study of J. Smith et al. (Coordination of Eating, Drinking and Breathing in Adults, John Smith, et. al., Chest, 1989, 96:33, 578-582), it was shown that swallowing occurred almost exclusively in expiration (in the study 271 patients were tested in which only two occurred in inspiration). This physiologic phenomenon is very important for a proper operation of the device provided by the present invention.

According to one embodiment of the present invention, a substance is released into the nasal passageways of a subject and does not reach the pulmonary region (which can occur while inspiring). According to J. Smith et al.'s research, there is a full coordination between drinking and breathing, such that when the subject is drinking a fluid, an inspiration is prevented, thus, at this stage, the substance can be safely released into the nasal passageways of the subject.

The present invention provides an air-intake actuated device adapted for delivering a substance to a nasal cavity of a subject, said device comprising (a) a container for containing said substance; (b) a nosepiece extending from said device for placement in proximity to a nose of said subject, said nosepiece being in fluid communication with said container; (c) a valve mechanically connectable to said container, characterized by at least two configurations: (i) an active configuration in which said valve enables delivery of predetermined amount of said substance from said container to said nasal cavity via said nosepiece; and, (ii) an inactive configuration, in which said valve prevents delivery of said predetermined amount of said substance from said container to said nasal cavity; (d) a mouthpiece extending from said device for placement in a mouth of said subject; and, (e) a trigger mechanism adapted to reconfigure said valve from said active configuration to said inactive configuration, and vice versa; wherein said trigger mechanism is activated by means of said subject intaking air through said mouthpiece; further wherein said trigger mechanism is adapted to reconfigure said valve from said inactive configuration to said active configuration for a predetermined period of time in response to said subject intake of air.

The present invention further provides a drinking-actuated device adapted for delivering a substance to a nasal cavity of a subject; the device comprising: (a) a container for containing said substance; (b) a nosepiece extending from said device for placement in proximity to a nose of said subject, said nosepiece being in fluid communication with said container; (c) a valve mechanically connectable to said container, characterized by at least two configurations: (i) an active configuration in which said valve enables delivery of predetermined amount of said substance from said container to said nasal cavity via said nosepiece; and, (ii) an inactive configuration; (d) a mouthpiece extending from said device for placement in a mouth of said subject; and, (e) a trigger mechanism adapted to reconfigure said valve from said active configuration to said inactive configuration, and vice versa; wherein said mouthpiece is fluidly connectable by means of a tubule to a fluid reservoir containing a fluid, said fluid reservoir is adapted to supply said fluid to said mouth of said subject via said mouthpiece; further wherein said trigger mechanism is adapted to reconfigure said valve from said inactive configuration to said active configuration for a predetermined period of time in response to a pressure gradient generated by suction applied by said subject to said tubule for drinking said fluid through said tubule.

FIG. 1 illustrates the pattern of breathing while drinking according to the study of J. Smith et al. The top graph illustrates tidal breathing, and the bottom graph illustrates the submental EMG (Electromyography), both related to the swallowing process. The arrows presented in the figure indicate swallows. The figure demonstrates that during drinking (the bottom graph) there is no change in the breathing pattern (upper graph). Hence it can be concluded that there is no breathing while drinking.

Figures 2A, 2B, 2C:
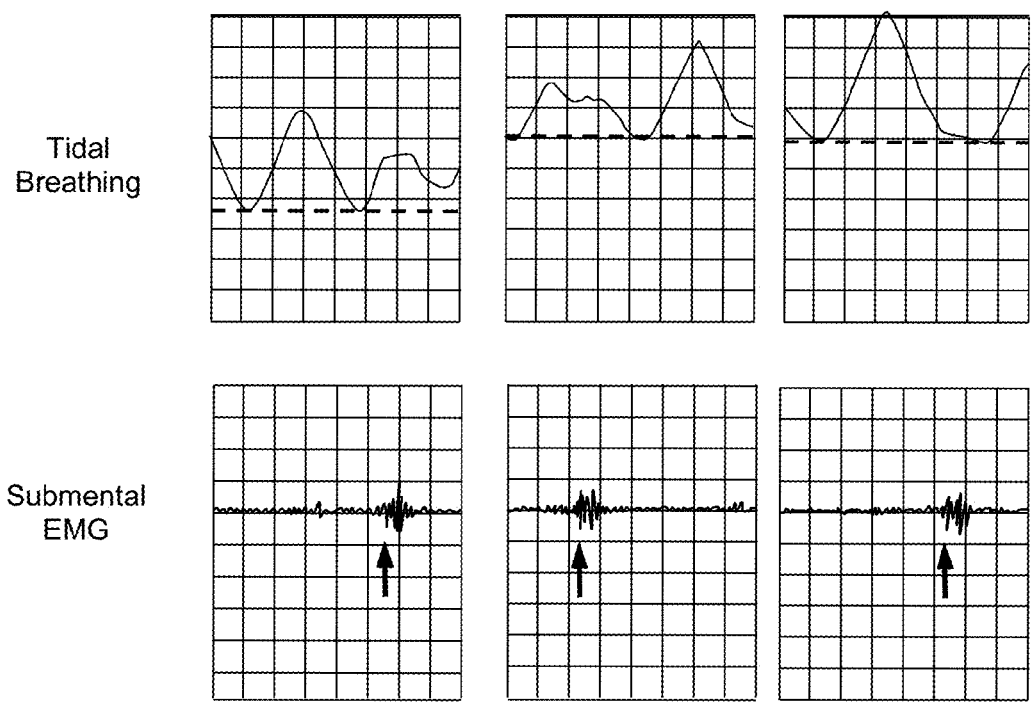
FIGS. 2*a-c* are an illustration of the pattern of swallowing and breathing according to the study of J. Smith et al.

The different patterns of swallowing and breathing were also studied by J. Smith et al., and are illustrated in FIGS. 2a-2c. As will be demonstrated, the inspiration is terminated while swallowing occurs. The top graphs illustrate the change in volume during tidal breathing, and the bottom graphs illustrate the submental EMG. In FIG. 2a, the swallow occurs at the beginning of expiration (end of inspiration). In the majority of swallows, as illustrated in FIG. 2b, the swallows occurred in midexpiration and were followed by further expiration. Occasionally, as illustrated in FIG. 2c, the swallows occurred close to the end of expiration, and were usually followed by further expiration. In each of the cases illustrated in FIGS. 2a-2c, breathing stops while swallowing occurs.

FIGS. 3a-3f schematically illustrate the motor events of the swallowing reflex (e.g., while drinking), on which the device of the present invention is based on.

Figures 3A, 3B, 3C:
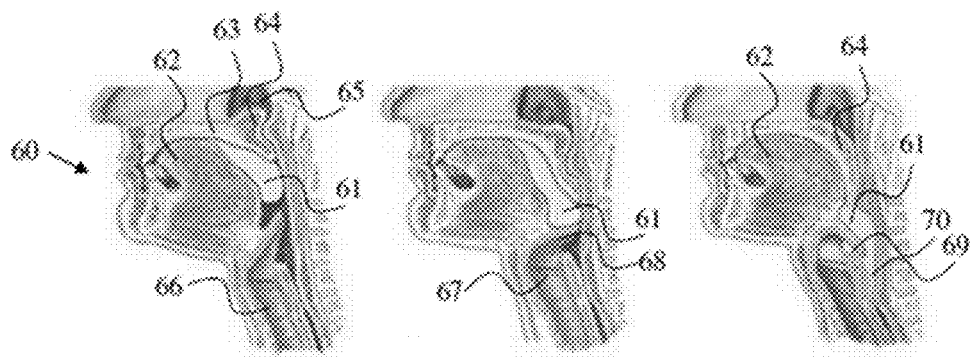
FIGS. 3*a-f* are a schematic illustration of the motor events of the swallowing reflex.

As was discussed above, there is ample evidence to suggest an important relationship between swallowing and breathing. Swallowing may be initiated by stimulation of many sites in the upper respiratory tract, though most studies suggest the epiglottis and larynx are the most sensitive areas for initiation of the swallowing reflex. FIG. 3a illustrates the onset of the swallowing reflex when a subject 60 swallows bolus 61 (e.g., water, food, etc.).

Said figure illustrates the tip of the tongue 62 in contact with the anterior part of the palate 63. The bolus 61 is pushed backward in groove between the tongue 62 and the palate 63. As a result, the soft palate 64 is being drawn upward, such that the nasal passageways 65 and the respiratory system 66 are isolated from each other.

As can be seen in FIG. 3b, the bolus 61 has reached the vallecula, the hyoid bone and the larynx 67 move upward and forward, the epiglottis 68 is tipped downward, and the contraction wave on posterior pharyngeal wall moves downward. As can be seen in FIG. 3c, the soft palate 64 has been pulled down and has been approximated to the root of the tongue 62 by contraction of the pharyngopalatine muscles, and by pressure of a descending pharyngeal contraction wave.

Following that, the cricopharyngeus muscle is opened to permit entry of the bolus into the esophagus 69, and the trickle of the bolus 61 enters also the laryngeal opening 70 but is prevented from going further by closure of the ventricular folds.

Figures 3D, 3E, 3F:
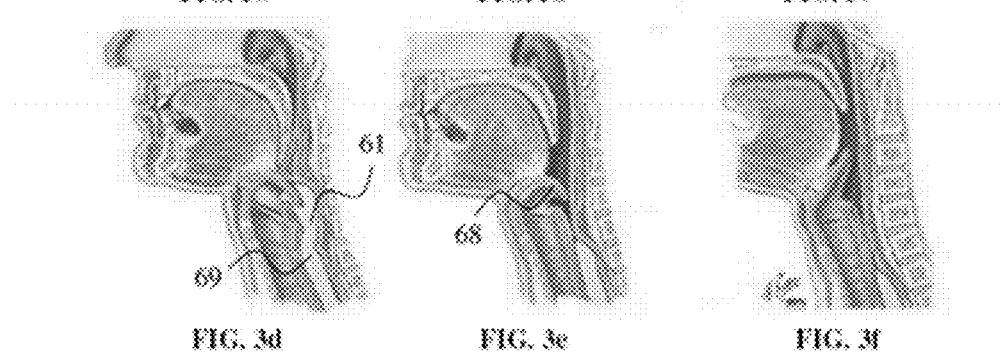

As can be seen in FIG. 3d, the contraction wave has reached the vallecula and is pressing out the remains of the bolus 61. Now the bolus has largely passed through the upper sphincter into esophagus 69. As can be seen in FIG. 3e, the contraction wave has passed the pharynx, the epiglottis 68 is beginning to turn up again as hyoid bone and the larynx descends. Now, the communication with the nasopharynx has been re-established.

In FIG. 3f, all structures of the pharynx have returned to resting position.

As was disclosed above, the present invention takes advantage of the physiological process illustrated in FIG. 3a-3f. When the soft palate is drawn upwardly and closes, a substance (e.g., a drug, a vaccine, etc.) can be delivered to the nasal passageways, without reaching the repository system and the lungs.

Reference is now made to FIG. 4a-4f which schematically illustrate the mechanism of a drinking-actuated substance delivery device 10 of the present invention and the action of the swallowing mechanism of a subject 90 according to some embodiments of the invention.

Figures 4A, 4B:
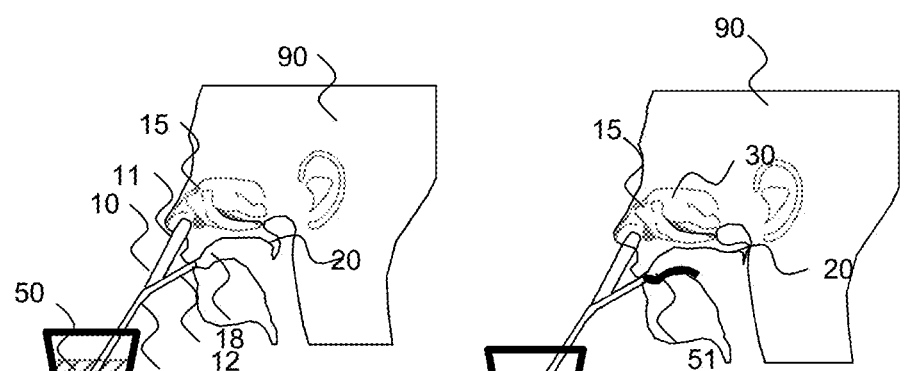
FIGS. 4*a-h* are a schematic illustration of the mechanism of a drinking-actuated substance delivery device of the present invention and the swallowing mechanism of a subject.

According to FIG. 4a, a nosepiece 11 of device 10 is inserted into the nose of subject 90, and mouthpiece 12 is inserted into said subject's mouth 18. According to said embodiments, device 10 is fluidly connected to fluid reservoir 50 (e.g., a bottle, a can, etc.) such that subject 90 drinks fluid 51 (e.g., water, a juice, a fluid medication, a cold fluid, a warm fluid etc.) through device 10. In FIG. 4a, the soft palate 20 of subject 90 is opened, such that subject 90 is able to breath. FIG. 4b illustrates the activation of device 10. When subject 90 begins to drink fluid 51, the swallowing reflex is activated, such that soft palate 20 is closed.

Simultaneously to the passage of fluid 51 within the throat of said subject, a predetermined amount of substance 15 is delivered from device 10 to nasal passageways 30 into the subject's nose.

Figures 4C, 4D:
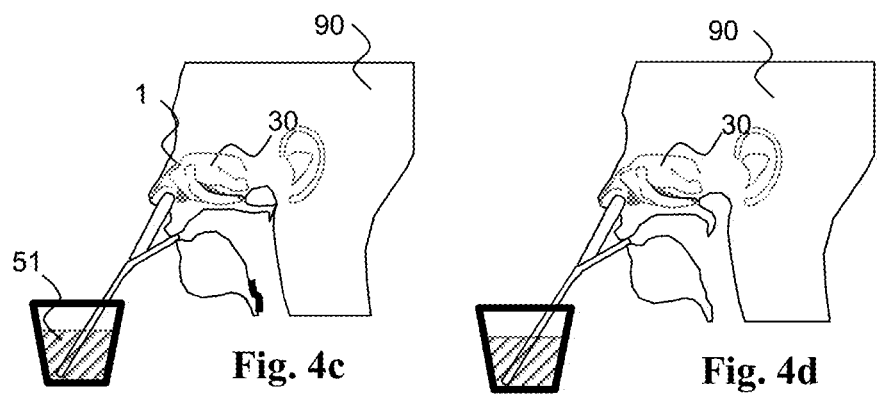

As illustrated in FIG. 4c, the subject had finished drinking said fluid and the substance 15 had been delivered to nasal passageways 30.

According to FIG. 4d, said fluid has been swallowed by subject 90, substance 15 has been already diffused within nasal passageways 30 and the soft palate is opened again.

Figures 4E, 4F:
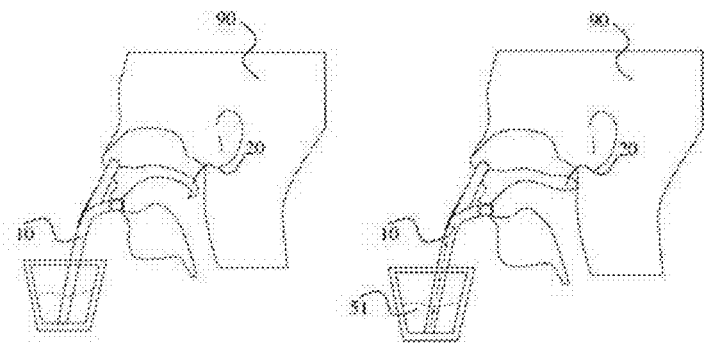

According to FIG. 4e, a nosepiece of the device 10 is inserted into the nose of subject 90, the mouthpiece is inserted into said subject's mouth, and the device is fluidly connected to the fluid reservoir (e.g., a bottle, a can, etc.) such that subject 90 is able to drink the fluid (e.g., water, a juice, a fluid medication, a cold fluid, a warm fluid etc.) through the device. In FIG. 4e, the soft palate 20 of subject 90 is opened, such that subject 90 is able to breathe.

FIG. 4f illustrates the activation of device 10. When subject 90 begins to drink fluid 51, the swallowing reflex is activated, such that soft palate 20 is closed.

Figures 4G, 4H:
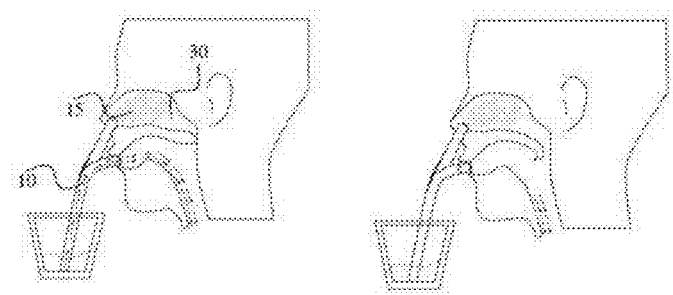

As illustrated in FIG. 4g, the subject is drinking said fluid and simultaneously a predetermined amount of substance 15 is delivered from device 10 to nasal passageways 30 into the subject's nose.

According to FIG. 4h, said fluid has been swallowed by the subject, substance 15 is in the process of diffusion within the nasal passageways and the soft palate is opened again.

Figure 5:
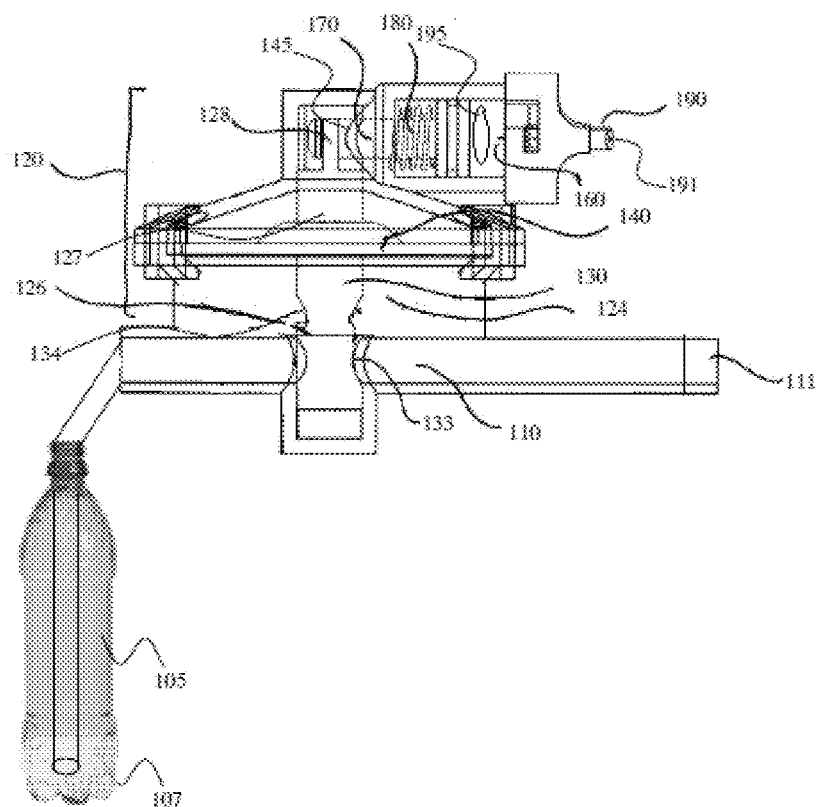
FIG. 5 is a schematic illustration of the drinking-actuated substance delivery device according to one embodiment of the present invention.

FIG. 5 schematically illustrates one embodiment of the drinking-actuated substance delivery device 200 for delivering a substance to a nasal cavity of a subject.

According to this figure, drinking-actuated device 200 comprises the following main element:

a. A container 195 for containing said substance (not shown).
b. A nosepiece 190 extending from drinking-actuated device 200 for placement in proximity to a nose of said subject. Nosepiece 190 is in fluid communication with container 195. The substance is adapted to be administrated through nosepiece 190 to the nose of the subject.
c. A valve 145 mechanically connectable to container 195. Valve 145 is characterized by at least two configurations:
   i. an active configuration in which valve enables the delivery of predetermined amount of substance from container 195 to the nasal cavity of the subject via nosepiece 190; and,
   ii. an inactive configuration in which the substance is not delivered to the nose of the subject.
d. A mouthpiece 111 extending from device 200 for placement in a mouth of the subject.
e. A trigger mechanism 120 adapted to reconfigure valve 145 from the active configuration to the inactive configuration, and vice versa; and
f. A tubule 110 fluidly connectable with mouthpiece 111 and a fluid reservoir 105 containing a fluid 107. Fluid reservoir 105 is adapted to supply fluid 107 to the mouth of the subject via mouthpiece 111.

According to some embodiments of the present invention, the trigger mechanism 120 which is adapted to reconfigure valve 145 from the inactive configuration to the active configuration for a predetermined period of time in response to a pressure gradient generated by suction applied to tubule 110 (through mouthpiece 111) while the subject sucks and drinks fluid 107 through tubule 110.

Trigger mechanism 120 is adapted to reconfigure valve 145 from the active configuration to the inactive configuration when the pressure gradient is absent.

According to some embodiments, valve 145 is reconfigurable from the inactive configuration to the active configuration when the pressure gradient applied is above a predetermined threshold.

According to the present invention, while using device 200, the substance is delivered to the nose of the subject while the same drinks fluid 107.

During the drinking of the fluid 107, the swallowing reflex is activated, and a result the soft palate of the subject is closed. During this process, the nasal cavity of the subject is substantially isolated from the remainder of the pulmonary system, so that the delivery of the substance to the nasal cavity may be performed safely.

According to some embodiments, the operation of nosepiece 90 and valve 145 is similar to an operation as known in the art as a spray device which is able to generate a spray effect on the target tissue.

According to a specific embodiment of trigger mechanism 120 which is illustrated in FIG. 5, trigger mechanism 120 comprises a controlling member 130 vertically positioned relatively to tubule 110.

Controlling member 130 has three main portions: a first end 126 positioned within tubule 110; a middle portion 127 in communication with a membrane 140; and, a second end 128.

As will be explained hereinafter, when second end 128 is in communication with valve 145, the valve is in the inactive configuration; and, when second end 128 of the controlling member is not in communication with valve 145, the to the valve 145 is reconfigured to the active configuration.

The connection of first end 126 of controlling member 130 and tubule 110 is performed through an aperture 133. First end 126 is reciprocally movable within tubule 110 and second end 128 is reciprocally movable within valve 145 in response to the pressure gradient.

Controlling member 130 has two configurations:
   i. a closed configuration (illustrated in FIGS. 5 and 6) in which fluid is not provided to the subject via tubule 110 and valve 145 is in the inactive configuration; and,
   ii. an opened configuration (illustrated in FIG. 7) in which the subject drinks fluid 107 through tubule 110 and valve 145 is in the active configuration.

According to different embodiments of the present invention, controlling member 130 may be positioned with respect to tubule 110 at any predetermined angle between about 5° and about 175°.

According to different embodiments of the present invention and the embodiment of FIG. 5, trigger mechanism 120 comprises a pressure responsive cavity 124 mechanically connected to controlling member 130 in middle portion 127.

Cavity 124 is a pressure responsive cavity which is adapted to reconfigure controlling member 130 from the closed configuration to the opened configuration, and vice versa.

When a pressure gradient is applied (i.e., when the subject sucks on tubule 110 through mouthpiece 111), the controlling member is reconfigures to the opened configuration, and when the pressure gradient is absent, the controlling member is reconfigured to the closed configuration.

In the closed configuration, controlling member 130 is adapted to block the passage of fluid 107 from fluid reservoir 105 to 111 mouthpiece through tubule 110.

The reconfiguration of connecting member 130 between the two configurations is performed via flexible membrane 140 which is an essential part of cavity 124.

Flexible membrane 140 is mechanically connected to connecting member 130 by surrounding the same in middle portion 127.

Flexible membrane 140 is adapted to change its shape (e.g., to an arched shape) in response to the pressure gradient in tubule 110. As a result of this shape change, controlling member 130 will be dragged towards tubule 110 and reconfigured from the closed configuration to the opened configuration.

Controlling member 130 comprises two apertures:
   (i) a first aperture 133 which is adapted to fluidly communicate between cavity 124 and mouthpiece 111 through at least a part of tubule 110. First aperture 133 is extendable within controlling member 130 from the area of tubule 110 to the area of cavity 124. First aperture 133 is adapted to 'transfer' the pressure gradient from said tubule 110 to cavity 124, such that controlling member 130 is reconfigured from the closed configuration to the opened configuration.
   (ii) A second aperture 134 adapted to facilitate passage of fluid 107 through controlling member 130 when controlling member 130 is in the opened configuration. Second aperture 134 is in fluid communication with the upper part of first aperture 133. While being in the opened configuration, the passage of fluid 107 within second aperture 134 is adapted to preserve controlling member 130 in this configuration as fluid 107 passes through controlling member 130.

According to the embodiment of FIG. 5, valve 145 comprises a spring 180 which is at least partially tensed in the inactive configuration of the valve, and at least partially released in the active configuration of the valve.

In the at least partially tensed position of spring 180, more static energy is stored within the spring relative to the at least partially released position of spring 180.

According to this embodiment, valve 145 further comprises a piston 170 to which spring 180 is connected. Piston 170 is adapted to push via spring 180 container 195 towards a needle 160. As result of this, the substance will be released to the patient through nosepiece 190.

In said inactive configuration, piston 170 is not pushing container 195. Furthermore, in said active configuration, in which spring 180 is released, the static energy stored within the spring is converted to a pushing energy actuated on container 195 via piston 170.

The reconfiguration of the valve from the inactive configuration to the active configuration is performed when second end 128 moved down as a result of the reconfiguration of connecting element 130 from the closed configuration to the opened configuration.

According to other embodiments, valve 145 may comprise a spring which is at least partially released in the inactive configuration, and at least partially tensed in the active configuration.

According to some embodiments, tubule 110 is at least partially a straw. According to other embodiments, the device of the present invention may be connected to a straw which may be inserted within the fluid reservoir.

According to the embodiment of FIG. 5, the operation of trigger mechanism 120 is synchronized with the drinking of fluid 107 by performed by the subject.

According to some embodiments, trigger mechanism 120 comprises a pulsation mechanism adapted to reconfigure valve 145 from the inactive configuration to the active configuration and vice versa in sequence of pulses, each of which is characterized by a predetermined length of pulse.

Valve 145 adapted to a release the predetermined amount of the substance according to the sequence of pulses. For example, in each pulse at least two doses of said predetermined amount of said substance are released.

According to some embodiments, nosepiece 190 may comprise a spray nozzle 191. According to some embodiments, the spray nozzle may be characterized by a diameter which influences said predetermined period of time.

Figure 6:
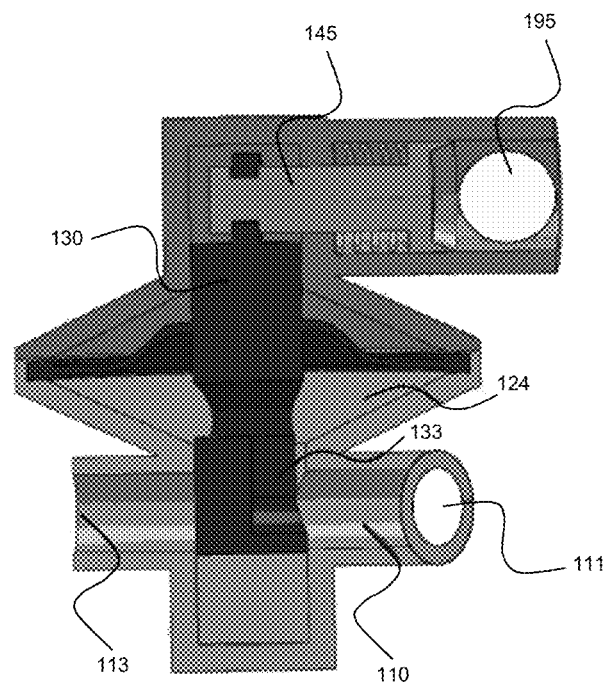
FIG. 6 is a schematic illustration of the a cross-section of the drinking-actuated substance delivery device according to another embodiment of the present invention.

Reference is now made to FIG. 6 which schematically illustrates a cross section of device 200. According to this figure, controlling member 130 is in the closed configuration, and a result of that, valve 145 is in the inactive configuration.

When a subject (not shown) drinks a fluid via tubule 110 and opening 113 and mouthpiece 111, a pressure gradient is formed within said tubule. Such fluid may be stored within a fluid reservoir (not shown). The pressure gradient which is formed within part of tubule 110 is delivered also to cavity 124 through first aperture 133.

Figure 7:
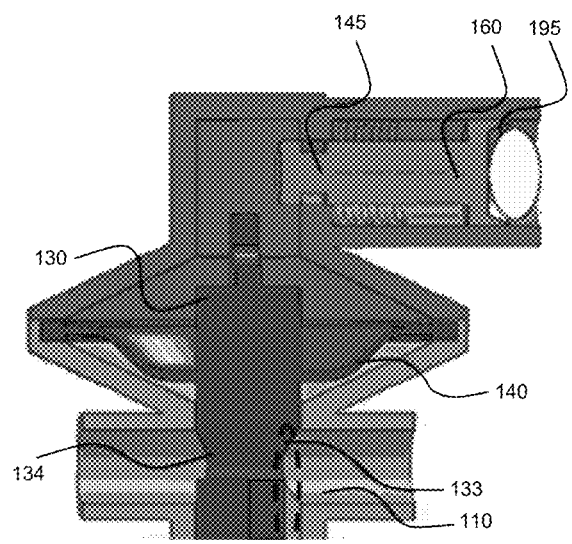
FIG. 7 is a schematic illustration of the a cross-section of the drinking-actuated substance delivery device according to another embodiment of the present invention.

Reference is now made to FIG. 7. According to this figure, as a result of the pressure gradient which is formed within cavity 124, flexible membrane 140 is moved downwards. As a result of that, controlling member 130 is dragged (by means of said membrane 140) to recess 138, and thus reconfigured from the closed configuration to the opened configuration.

In the opened configuration, the following two features occur:

1) The fluid flows within tubule 110 through first end 126 of controlling member 130.

2) As a result of the movement of the controlling member 130 and hence the second end 128 (e.g., a safety catch), the valve 145 is reconfigured from the inactive configuration to the active configuration. As a result of that, the substance is delivered from container 195 to the nasal cavity of the patient via nosepiece (not shown).

According to some embodiments, the substance can be stored within container 195 under a predetermined pressure. Therefore, when needle 160 contacts a specific point in container 195, the substance may be released (e.g., as a spray).

According to some embodiments, valve 145 may comprise more than one element which reconfigures it to the active configuration.

According to other embodiments, container 195 is a syringe.

According to other embodiments, device 200 may further comprise a cap which is adapted to cover at least a portion of the components of said device for sterilization/aseptic purposes. This cap may comprise an opening.

According to some embodiments, container 195 is adapted to be connected to an external container (not shown). The external container is adapted to fill container 195 with a predetermined dose of a substance.

According to some embodiments, device 200 may further comprise indicating means adapted to indicate the amount of said substance within said container. The indicating means may be a transparent window located on a side of the container.

According to some embodiments, fluid 107 may be selected from a group consisting of: water, a juice, a fluid medication, a cold fluid, a warm fluid, or any combination thereof.

Reference is now made to FIG. 8 which schematically illustrates a specific embodiment of device 300 according to the present invention.

According to this figure, device 300 comprises a nosepiece 290, a mouthpiece 211, a tubule 210, and a triggering mechanism 220.

According to this embodiment, the device 300 comprises a recess 238 to which the controlling member (not shown) enters when it reconfigured from the closed configuration to the opened configuration (so as to reconfigure the valve from the inactive configuration to the active configuration).

The edge 212 of tubule 210 may be inserted into a fluid reservoir (not shown). Reference is now made to a specific embodiment of controlling member 130. According to this embodiment, controlling member 130 has three main portions: a first end 126; a middle portion 127; and, a second end 128.

The first end 126 is adapted to be placed within tubule 110. The middle portion 127 is adapted to be connected to membrane 140. The second end 128 is adapted to be reversibly connected to valve 145.

First end 126 is reciprocally movable within tubule 110 and second end 128 is reciprocally movable with respect to valve 145 in responsive to the pressure gradient generated within tubule 110.

FIG. 9 provides a better view of the first aperture 133 and the second aperture 134.

First aperture 133 is adapted to be in fluid communication with the cavity 124 and the mouthpiece 111 through a portion of tubule 110.

First aperture 133 extends within controlling member 130 from the area of tubule 110 to the area of cavity 124. First aperture 133 is adapted to transmit the pressure gradient from said tubule 110 to cavity 124 (once the user sucks/ drinks the fluid), such that controlling member 130 is reconfigured from the closed configuration to the opened configuration.

Second aperture 134 is adapted to facilitate passage of fluid 107 through controlling member 130 when controlling member 130 is in the opened configuration.

Second aperture 134 is in fluid communication with the upper part of first aperture 133. While the controlling member 130 is in the opened configuration, the passage of fluid 107 thought second aperture 134 is adapted to preserve and maintain the controlling member 130 in the opened configuration.

FIG. 10 illustrates another embodiment of several parts of the device according to the present invention. In this figure the following components are illustrated: controlling member 130, tubule 110, and mouthpiece 111.

Figure 11:
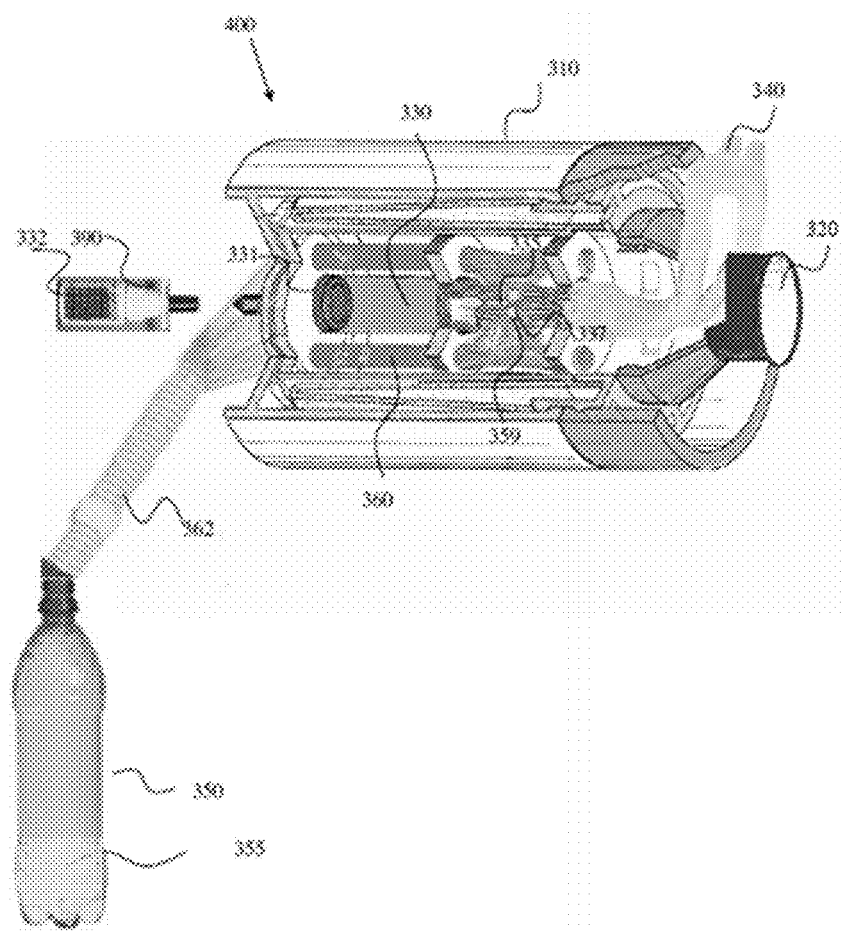
FIG. 11 is a schematic illustration of the drinking-actuated substance delivery device according to another embodiment of the present invention.

Reference is now made to FIG. 11 which schematically illustrates another embodiment of the drinking-actuated substance delivery device 400.

The drinking-actuated device 400 includes housing 310, having a mouthpiece 320 which extends out from device 300.

Mouthpiece 320 is adapted to be placed in a mouth of a subject. Housing 310 also contains container 330 which is adapted to contain substance 332 (e.g., a drug, a vaccine, etc.).

Container 330 is in a fluid communication with nosepiece 340 through valve 335.

Nosepiece 340 extends from device 400, and is adapted to be placed in or around a nose of a subject.

Valve 335 is adapted to regulate passage of substance 332 from container 330 to nosepiece 340. The operation of valve 335 is performed by trigger mechanism 337 which is adapted to transform valve 335 from an inactive configuration to an active configuration, and vice versa.

According to the present invention, device 400 is fluid-based actuated. I.e., while a subject drinks a fluid (e.g., juice, water, etc.) 355 through device 400.

Fluid 355 is supplied from a fluid reservoir 350 (e.g., a bottle, a can, etc.) to mouthpiece 320, which is fluidly connected to fluid reservoir 350 by means of tubule 360.

While a subject (e.g., user, patient, etc.) drinks fluid 355, the fluid flows in tubule 360. Such flow creates pressure within said tubule.

Said pressure in tubule 360 actuates a trigger mechanism 337 in actuation point 359, such that the actuated trigger mechanism 337 opens valve 335 to a predetermined period of time.

The result of that is the following: a predetermined amount of substance 332 is released from container 330 to nosepiece 340 when said pressure is greater than a predetermined pressure threshold.

The pressure threshold is the minimum pressure needed to activate trigger mechanism 337 and is in the range of about 0.1 Pascal to about 30 Pascal.

According to some embodiments, trigger mechanism 337 is synchronized with the drinking of fluid 355 by the subject. According to the preferred embodiment of the invention, fluid 355 which is drunk by the subject activates the swallowing reflex that closes the soft palate for a specific period of time, such that the nasal passageways of said subject's nose are substantially isolated from the remainder of the pulmonary system. At this specific period of time, the substance is released from the device to the nasal passageways. According to some embodiments, the release of said substance is simultaneous with the drinking and swallowing of said fluid.

According to some embodiments, trigger mechanism 337 is incorporated within valve 335, such that there is one valve which is responsive to an external pressure of fluid and is responsible for releasing the substance to the nosepiece.

According to some embodiments, the actuation of the valve by the trigger mechanism is at least partially based on the Venturi effect. This effect is based on the Bernoulli equation which states that the sum of all forms of energy in a gas flowing along an enclosed path is the same at any two points in that path (or streamline) Its formulation in the simple hypothesis of incompressible flow (gas motion with negligible changes in density) is:

$$\frac{v^2}{2} + gh + \frac{p}{\rho} = const.$$

where: v is the gas velocity along the streamline, g is the acceleration of gravity on Earth, h is the height, p is the pressure along the streamline, and ρ is the gas density. As a consequence of Bernoulli's law, a gas passing through smoothly varying constrictions is subjected to changes in velocity and pressure. A Venturi is a system for speeding the flow of the gas, by constricting it in a cone shaped tube. In the restriction, the fluid must increase its velocity, reducing its pressure and producing a vacuum. As the gas leaves the constriction, its pressure increases back to the ambient or pipe level.

The opening of valve 335 is also influenced by the amount of substance which is released and the inspiratory force with which the subject is drinking the fluid. According to the Venturi effect, the amount of substance and the inspiratory force, or at least part of them, create the predetermined pressure threshold mentioned above.

In order to reconfigure valve 335 to the active configuration, the pressure in tubule 360 has to be greater than this pressure threshold, such that trigger mechanism 337 is actuated and valve 335 is actuated for a predetermined period of time.

The drinking-actuated mechanism of the device of the present invention has the ability to eliminate bad flavor of the substance which is released into the subject's nose by combining the release of the substance in the nose with a "throat washing" effect by the fluid which is simultaneously drunk by the subject. According to some embodiments of the invention, tubule 360 can be at least partially a straw.

According to the preferred embodiment of the invention, tubule 360 is fluidly connected to an external straw 362. According to some embodiments, straw 362 is insertable into fluid reservoir 350.

According to some embodiments of the invention, container 330 of device 400 may comprise a piston 131 which is adapted to compress substance 332 within the container 330. Such a compression creates pressure within container 330 and pushes said substance 332 forward. In a preferred embodiment of the invention, piston 331 is located in the back side of container 130.

According to some embodiments, trigger mechanism 337 is adapted to reciprocally move piston 331 within container 330, when it is actuated in response to the fluid 355 pressure within the tubule 360 while the subject drinks the fluid.

According to some embodiment of the invention, trigger mechanism 337 comprises a pulsation mechanism which is adapted to actuate valve 335 in a predetermined sequence of pulses.

Each pulse is characterized by a predetermined length of pulse (in time) in which a predetermined amount of said substance is released by said valve according to said sequence of pulses.

For example, the subject drinks the fluid so as to actuate the trigger mechanism for a total amount of 4 seconds.

In this case, two doses of substance can be sprayed into the nose, the first dose between the first second and the second one, and the second dose between the third second and the fourth second.

According to some embodiments, nosepiece 340 is in fluid communication with valve 335 by means of a spray nozzle. In this case, the spray nozzle might be a known in the art spray nozzle which is able to release the substance by spraying it into the nose. According to these embodiments, the spray nozzle might be characterized by a diameter, which influences the predetermined period of time in which the substance released to the nose. According to some embodiments, container 330 is a syringe.

According to some embodiments, device 400 might comprise a cap which is adapted to cover at least a portion of the components of said device for sterilization/aseptic purposes. For example, a cap that covers the nosepiece, and/or the mouthpiece. This cap might comprise an opening.

The cap can be breakable upon reconfiguration of valve 145 from said inactive configuration to the active configuration, at a predetermined pressure. In other words when the device is being activated pressure is being built within the device. When said pressure reaches a predetermined pressure—the cap breaks\torn.

According to one embodiment of the present invention, the device 400 is utilized for a single use (namely a disposable device). According to another embodiment of the present invention, the device 400 is utilized for multiple uses.

According to a preferred embodiment of the invention, as illustrated in FIG. 11, device 400 might be mechanically connected (e.g., by piercing means) to external container 390. External container 390 is adapted to fill container 330 with substance 332.

According to some embodiments, external container 390 adapted to fill container 330 with a predetermined and a specific dose of said substance, for example, when the subject presses of the substance releasing part of the external container.

According to another embodiment, the substance 332 is already provided within container 330.

According to some embodiments, device 400 might comprise indicating means which are adapted to indicate the amount of substance within the container.

According to some embodiments, the indicating means is a transparent window located on a side of the container.

According to some embodiments, the substance implemented by the device of the present invention may be a drug selected from a group consisting of: Anti-Angiogenesis agents, Antisense, anti-ulcer, butorphanol, Calcitonin and analogs, Cyclooxygenase (COX-II) inhibitors, desmopressin and analogs, dihydroergotamine, Dopamine agonists and antagonists, Enkephalins and other opioid peptides, growth hormone and analogs, growth hormone releasing hormone, Growth hormone antagonists, IgE suppressors, Insulin, insulinotropin and analogs, Ketamine, Kytril (granisetron), Leutenizing hormone releasing hormone and analogs, lidocaine, metoclopramide, Midazolam, Narcotic analgesics, neuraminidase inhibitors, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, vasopressin, or any combination thereof.

According to some embodiments, the substance implemented by the device of the present invention may be a vaccine with or without carriers and/or adjuvants selected from the group consisting of: Prophylactics and therapeutic antigens, subunit protein, peptide and polysaccharide, polysaccharide conjugates, toxoids, genetic based vaccines, live attenuated reassortant, inactivated whole cells, viral and bacterial vectors for the treatment of arthritis, *Lactobacillus* species: *Lactobacillus acetotolerans, Lactobacillus acidifarinae, Lactobacillus acidipiscis, Lactobacillus acidophilus* (Doderlein bacillus), *Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustorum, Lactobacillus curvatus, Lactobacillus delbrueckii, Lactobacillus delbrueckii* subsp. *Bulgaricus, Lactobacillus delbrueckii* subsp. *Lactis, Lactobacillus diolivorans, Lactobacillus equi, Lactobacillus equigenerosi, Lactobacillus farraginis, Lactobacillus farciminis, Lactobacillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus hammesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefiranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae, Lactobacillus zymae,* Probiotics selected from a group consisting of Lactic acid bacteria (LAB) and bifidobacteria or any combination thereof; said substance is used for the treatment of at least one selected from a group consisting of cholera, *moraxella catarrhali*, cocaine addiction, *Haemophilus influenzae* type b (Hib), meningococcus, measles, mumps, rubella, varicella, yellow fever, Respiratory syncytial virus, pneumococcus, *streptococcus*, typhoid, influenza, hepatitis, including hepatitis A, B, C and F, polio, human immunodeficiency virus (HIV), parainfluenza, rotavirus, cytomegalovirus (CMV), *chlamydia*, non-typeable *haemophilus, moraxella catarrhalis*, human papilloma virus, tuberculosis including *Bacillus* Calmette-Guerin (BCG), gonorrhoea, asthma, atheroschlerosis, malaria, otitis media, *E-coli*, Alzheimer's disease, *H. Pylori, salmonella*, diabetes, cancer, herpes simplex, *Staphylococcus aureus, Streptoccocus*, or any combination thereof.

According to some embodiments, the substance implemented by the device of the present invention is used for the treatment of at least one selected from a group consisting of cholera, *moraxella catarrhali*, cocaine addiction, Hib, meningococcus, measles, mumps, rubella, varicella, yellow fever, Respiratory syncytial virus, pneumococcus, *streptococcus*, typhoid, influenza, hepatitis, including hepatitis A, B, C and F, polio, HIV, parainfluenza, rotavirus, CMV, *chlamydia*, non-typeable *haemophilus, moraxella catarrhalis*, human papilloma virus, tuberculosis including BCG, gonorrhoea, asthma, atheroschlerosis, malaria, otitis media, *E-coli*, Alzheimer's disease, *H. Pylori, salmonella*, diabetes, cancer, herpes simplex, *Staphylococcus aureus, Streptoccocus*, or any combination thereof.

According to some embodiments, the substance is a peptide or protein therapeutic agent such as cytokines, hormones, clotting factors, vaccines, monoclonal antibody.

According to some embodiments, the device is used for the treatment of central nervous system (CNS) disorders, brain disorders such as: brain cancer, acute brain injury, spinal cord injury, Alzheimer's disease, Neurogenesis, Parkinson's disease, depression, Epilepsy, schizophrenia by the delivery of substances such as: Neurotrophins, brain-derived neurotrophic factor (BDNF), glial cell-derived neurotrophic factor (GDNF), anti-epidermal growth factor receptor antibodies (anti EGF receptor AB), Enzymes such as Lysosomal enzyme, Neuregulin.

According to some embodiments, the substance implemented by the device of the present invention is selected from a group consisting of natural oils; Mint oils, Peppermint oil, Spearmint oil, Menthol, Olive oil, *Eucalyptus* oil, Amino acids, fatty acids and any combination thereof.

According to some embodiments, the substance implemented by the device of the present invention may be a therapeutic substance selected from a group consisting of: Agents for the common cold, Anti-addiction, anti-infectives, analgesics, anesthetics, anorexics, antiarthritics, anti-allergy agents, antiasthmatic agents, anticonvulsants, anti-depressants, antidiabetic agents, anti-depressants, anti-diuretics, anti-emetics, antihistamines, anti-inflammatory agents, antimigraine preparations, antimotion sickness preparations, antinauseants, antineoplastics, anti-obesity, antiosteoporeteic, antiparkinsonism drugs, antipruritics, antipsychotics, antipyretics, anticholinergics, benzodiazepine antagonists, bone stimulating agents, central nervous system stimulants, hormones, hypnotics, immunosuppressives, prostaglandins, proteins, peptides, polypeptides and other macromolecules, psychostimulants, rhinitis treatment, sedatives, sexual hypofunction, tranquilizers and vitamins including B12, probiotics, natural oils, natural ingredients, or any combination thereof.

As mentioned above, the particle's or droplet's size has significant impact on absorption when administering substance via the nose and the nasal epithelia. According to another embodiment of the present invention the particle's or droplet's size is in the micrometer and nanometer size.

The above disclosure is based on the user sucking (and drinking) liquid (e.g., water, juice etc.).

Figure 12:
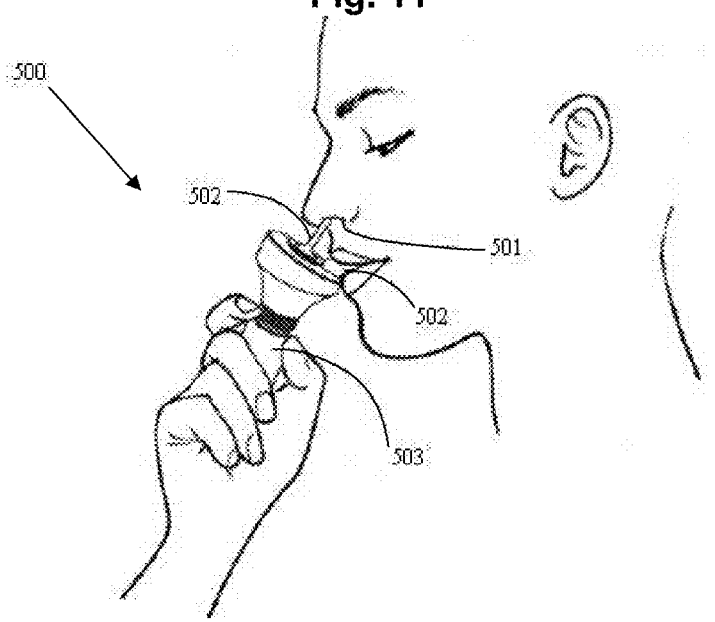
FIG. 12 illustrates another embodiment of the present invention in which an inhaling-actuating device 500 is presented.

According to another embodiment of the present invention, the mechanism is based on the user inhaling air (instead of in taking fluid). Reference is now being made to FIG. 12 which generally illustrates the above principle.

FIG. 12 illustrates the inhaling-actuating device 500 for delivering a substance to a nasal cavity 501 of a subject. The device generally comprises a mouthpiece 502 (through which the patient inhales and thus activates the mechanism), a container 503 accommodating a medicament to be delivered to said patient and a nose piece 504 adapted to dispense the medicament to the nasal cavity of the patient.

Reference is now made to FIGS. 13-14 which generally illustrate the basic concept behind the idea. FIG. 13 illustrates the mouth piece 502 of the inhaling-actuating device 500 placed within the mouth of the patient and the nose piece 504 placed within the nose of the patient.

FIG. 14 illustrates the inhaling-actuating device 500 once the same is activated, namely, once the patient takes in (or sucks) air. As will be described hereinafter, once the patient takes in air 505 the inhaling-actuating device 500 is activated and the medicament 506 is released to the nose 501 of the patient.

Reference is now being made to FIGS. 15-19b, illustrating a first specific mechanism of the inhaling-actuating device 500 as described above.

FIG. 15 illustrates the inhaling-actuating device 500 prior to the activation of the same (i.e., the air inhaling).

As can be seen in FIG. 15, the device comprises the nose piece 504 (to be placed within the nasal cavity of the patient), the mouth piece 502 (to be placed within the mouth of the patient, and a container 503 for accommodating the medicament 506 to be delivered to the nasal cavity of the patient. The actuation mechanism (for activating the device and delivering medicament to the patient's nasal cavity) comprises a first unidirectional valve 507, a membrane 508, an intermediate compartment 511 (for accommodating a uni-dose amount of medicament to be delivered to the patient's nasal cavity), at least one spring 509 and a second valve means 510.

Prior to the actuation of device 500, the unidirectional valve 507 enables filling of intermediate compartment 511 with the uni-dose amount of medicament 506. As will be described hereinafter, this is enabled due to the fact that after said medicament is released to the nasal cavity, vacuum is created in said intermediate compartment 511, which 'draws' said medicament 506 through unidirectional valve 507).

Figures 16A, 16B:
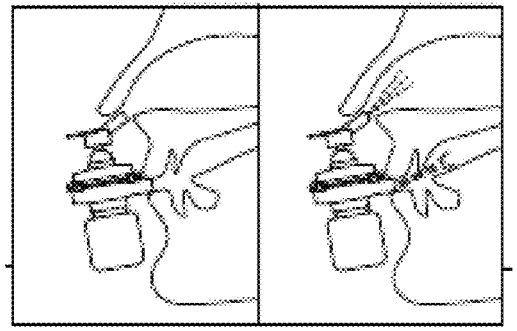
Figure 17:
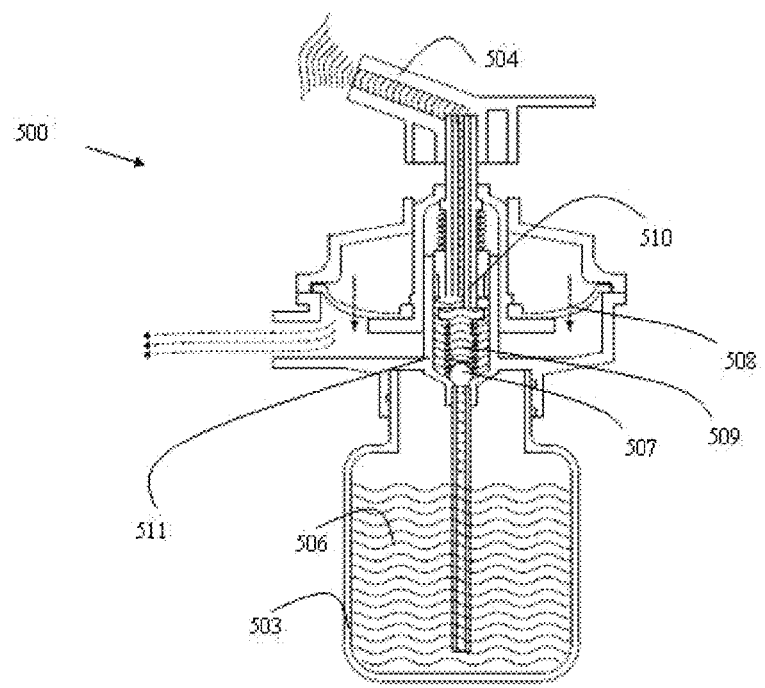

FIG. 16a illustrates the device 500 in place in the nose and mouth of the patient. FIG. 16b illustrates the activation of the device 500, namely, the sucking of air through mouth piece 502.

Reference is now being made to FIGS. 17-19b, illustrating the actuation mechanism. Once the patient takes in air (through mouthpiece 502) membrane 508 is drawn downwardly (in the direction of container 503. Membrane 508 is in communication with said spring 509; such that, when membrane 508 is drawn downwardly, said spring 509 is loaded and compressed.

Said spring 509 is in physical communication with valve means 510 such that, when spring 509 is loaded and compressed (as a result of the downwards movement of the membrane 508) valve means 510 are opened and the medicament 506 are released to the patient's nasal cavity.

It should be pointed out that valve means 510 additionally comprises sealing means 512 adapted to prevent the passage of medicament from the intermediate compartment 511 to the nasal cavity without the actuation of the patient (i.e., air suction).

Once the medicament is released to the nasal cavity, vacuum is created in the intermediate compartment 511, which eventually enables the withdrawal of another uni-dose amount of medicament 506 from the container 503 through unidirectional valve 507.

Figure 18A:
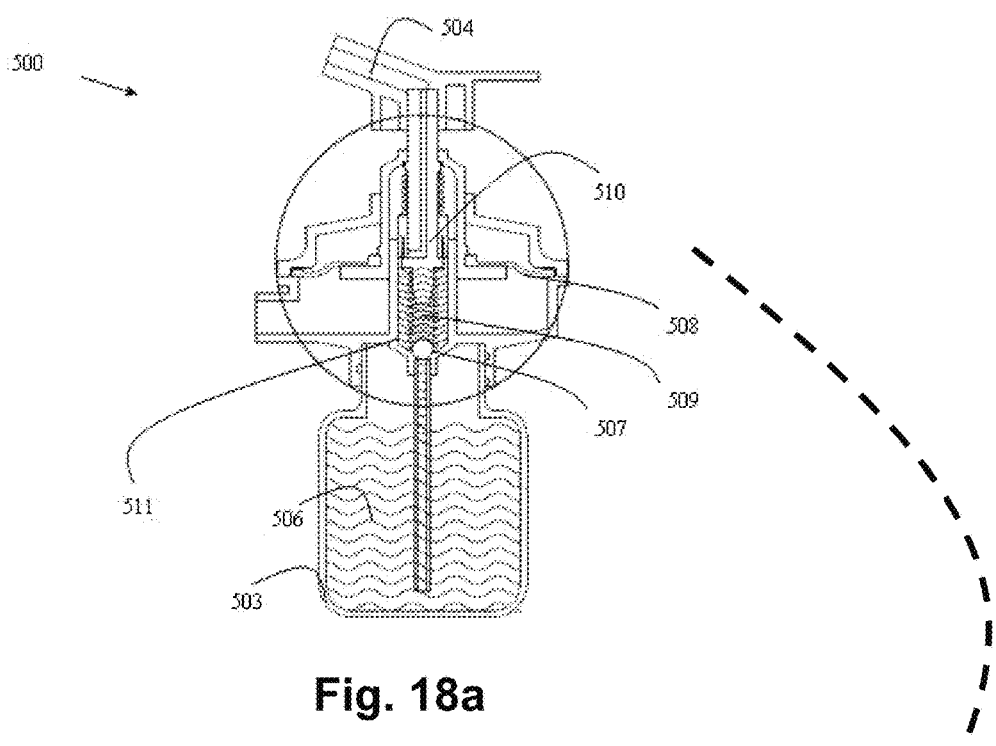
Figure 18B:
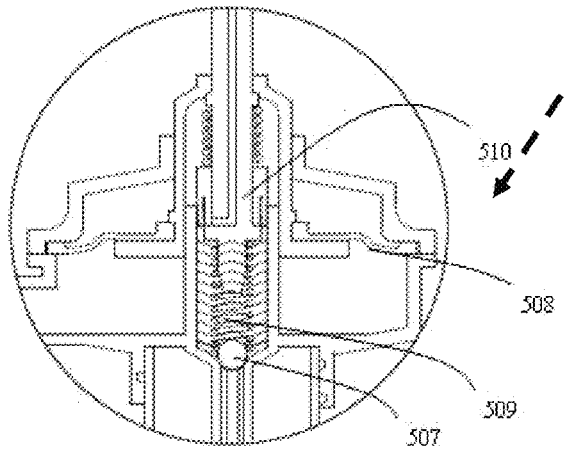
Figure 19A:
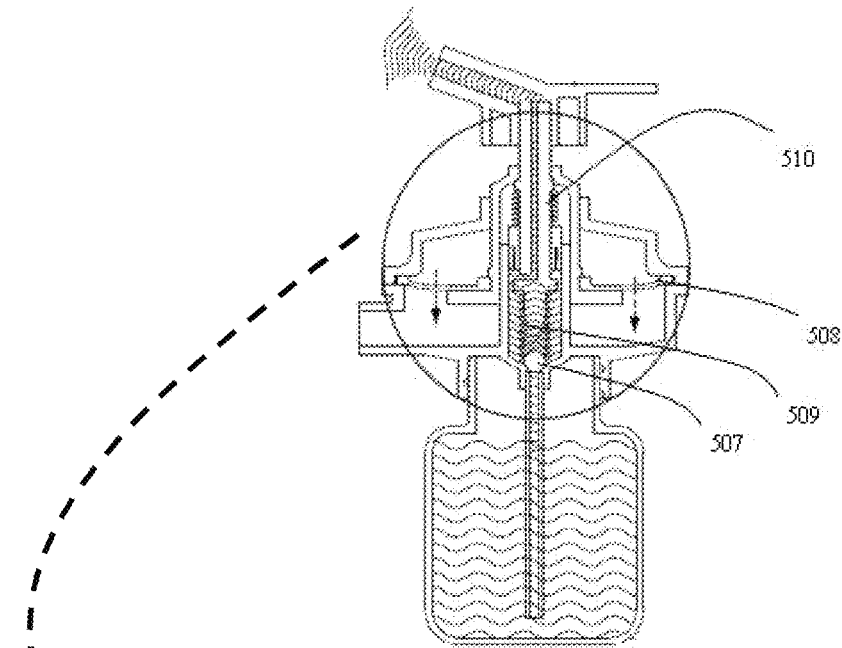
Figure 19B:
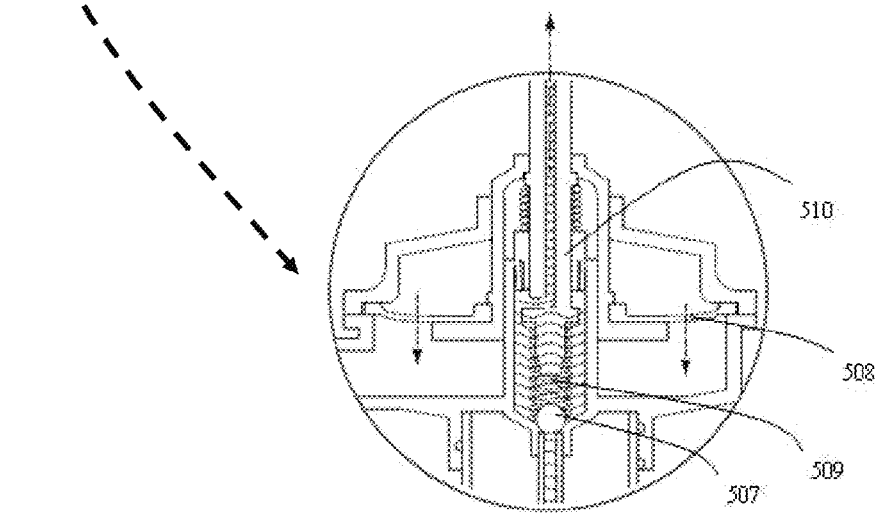

Reference is now made to FIGS. 18a-18b and 19a-19b which provide a closer view of the actuation step of device 500. FIGS. 18a-18b illustrates the device 500 prior to the actuation step and FIGS. 19a-19b illustrate the device 500 post-actuation.

As mentioned above, prior to the actuation, intermediate compartment 511 is filled with a uni-dose amount of medicament. In this stage, the valve means 510 is closed and sealing means 512 seals said intermediate compartment 511, preventing release of medicament to the patient.

FIGS. 19a-19b illustrates the device 500 post-actuation. As mentioned above, once the patient takes in air, membrane 508 is actuated and withdrawn downwardly such that spring 509 is loaded and compressed. Once spring 509 is compressed, valve 510 is opened and the medicament is released from the intermediate compartment 511 to the nasal cavity.

Reference is now made to FIGS. 20-26d which illustrate a second embodiment 600 of the above mentioned concept.

According to this embodiment, there is a further step of 'charging' or 'loading' the inhaling-actuating device 600 with the uni-dose amount of medicament 506.

Figure 20:
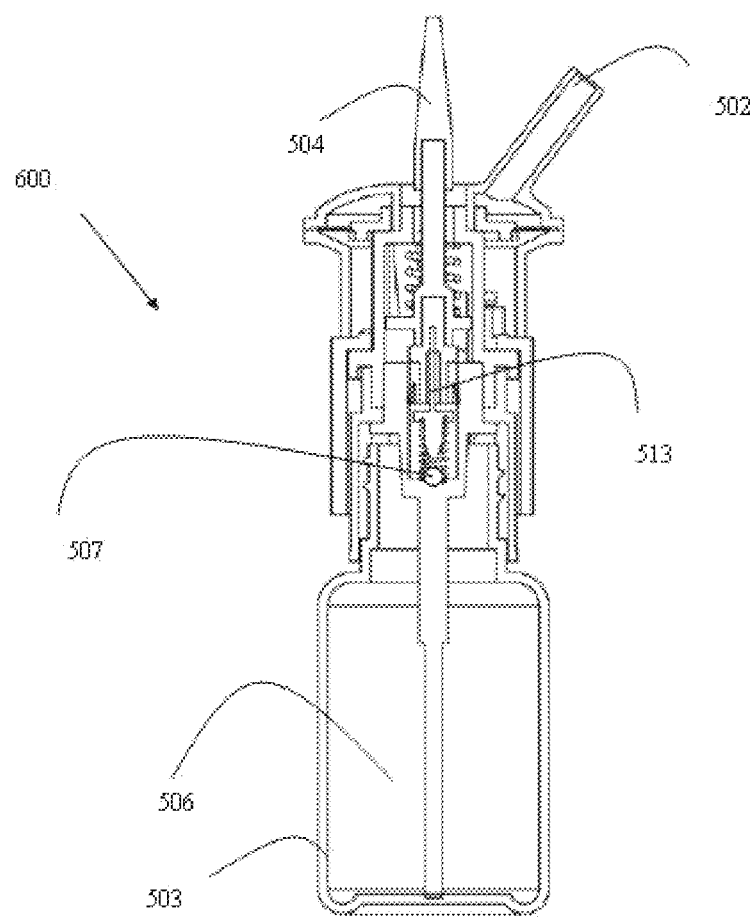
FIGS. 20-26e illustrate a second embodiment 600 of the present invention.

Reference is now made to FIG. 20 which illustrates the main components of inhaling-actuating device 600, which comprises a mouthpiece 502, a nosepiece 504, a unidirectional valve 507, a container 503 for accommodating the medicament 506 and a loading mechanism 513.

Figure 21:
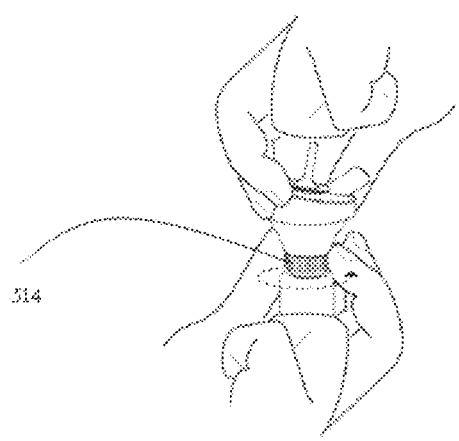
Figure 22A:
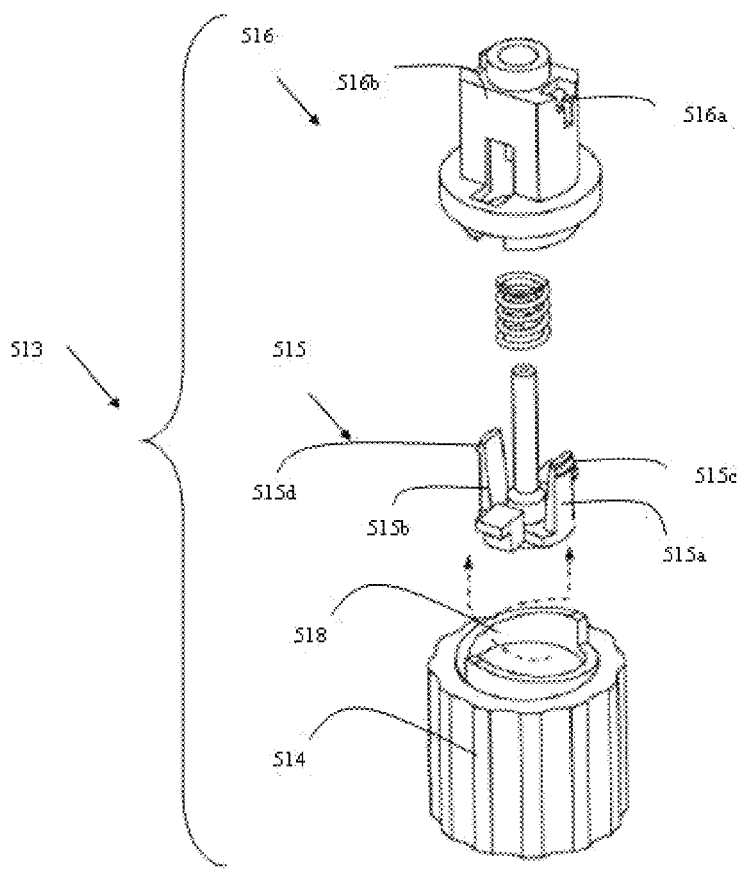
Figures 22B, 22C:
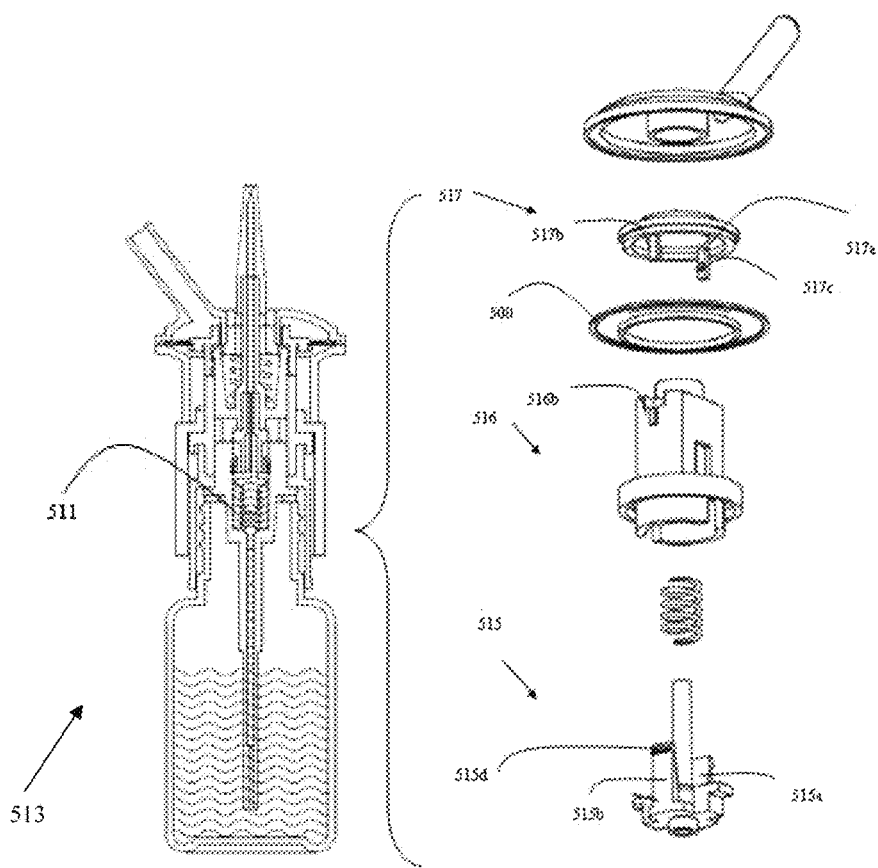

Reference is now made to FIG. 21 and FIGS. 22a-22c which provides a closer view of the loading mechanism 513. As can be seen in FIGS. 22a-22b, the loading mechanism 513 comprises a rotating knob 514, a first actuator 515 and a second actuator 516, complementary to said first actuator.

When the user wishes to load the device 600, he rotates knob 514 (see FIG. 21). Said rotating knob comprises a spiral elevating means 518 in communication with said first actuator 515. Rotation of the rotating knob 514 rotates the spiral elevating means 518 which eventually elevates the first actuator 515 and pushes the same into the complementary second actuator 516.

The first actuator 515 is characterized by at least two wings 515a and 515b, each of which comprises a protrusion (i.e., a bulge) 515c-515d, respectively.

Said complementary second actuator 516 comprises two grooves 516a and 516b adapted to accommodate said bulge 515c and 515d.

Said complementary second actuator 516 is further coupled to a third complementary actuator 517. Said third complementary actuator 517 comprises, like actuator 515, at least two wings 517a and 517b, each of which comprises a protrusion (i.e., a bulge) 517c and 517d (517d is not shown), respectively.

Once said rotating knob 514 is rotated and the first actuator is elevated into the complementary second actuator 516 and into the third complementary actuator 517; bulges 515c and 515d are positioned inside grooves 516a-516b of the second actuator 516. Bulges 515c and 515d are held in place by bulges 517c and 517d of the third complementary actuator 517 (see FIGS. 22a-22b).

Such movement of said actuator creates vacuum inside the intermediate compartment 511, and thus, the device 600 is loaded with the dose to be delivered to the patient (see FIG. 22c).

Figure 23:
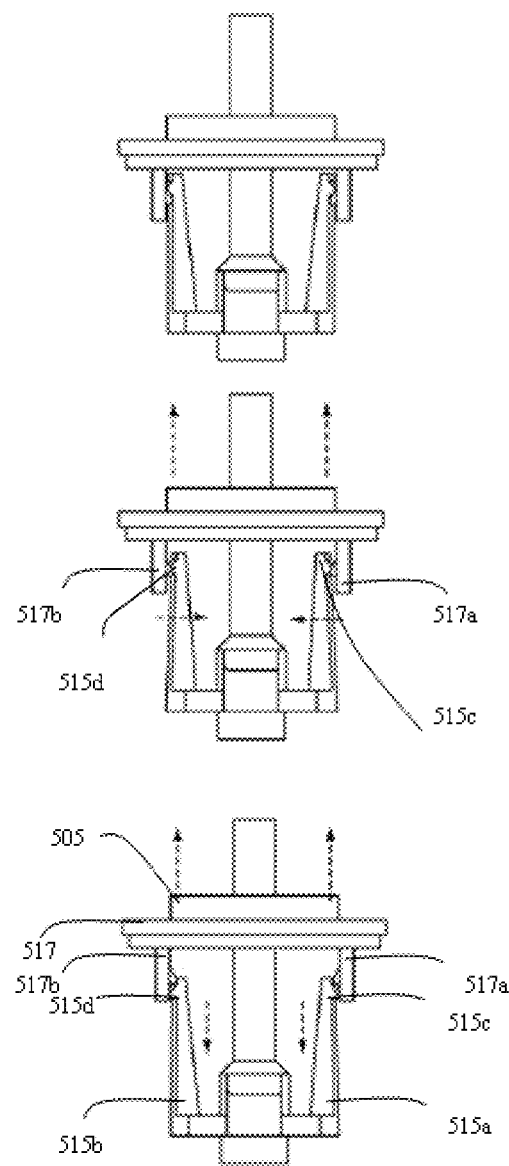
Figure 24:
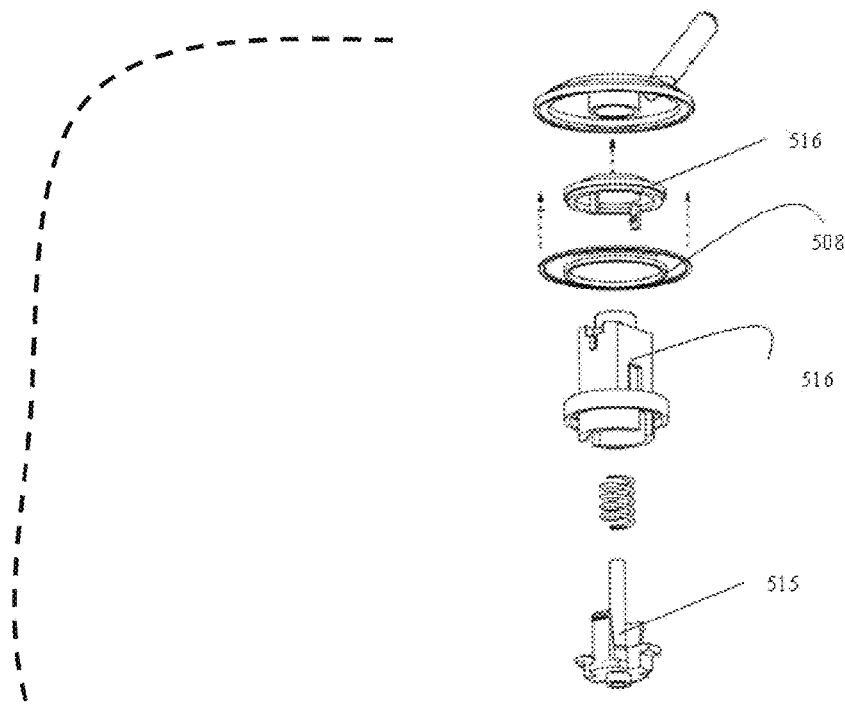
Figure 25:

Reference is now made to FIGS. 23-25 which illustrate the activation of device 600 (namely, air intake by the user, as seen in FIG. 25). When the user takes in air, the medicament 506 is released to the user and membrane 508 is elevated upward. Said membrane is coupled to said third complementary actuator 517.

Once said membrane 508 is elevated, said third complementary actuator 517 is elevated as well. Said elevation pushes said wings 517a and 517b inward so as to release said wings 515a and 516b of actuator 515. And thus, to return actuator 515 to its initial potion (the pre-loading position).

Figure 26A:
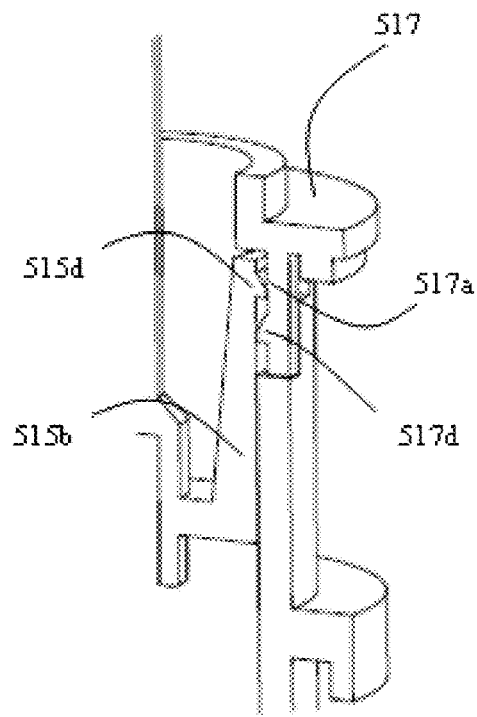
Figure 26B:
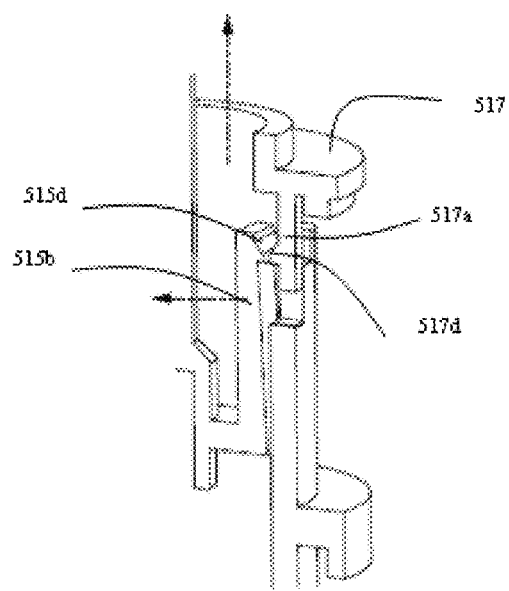
Figures 26C, 26D:
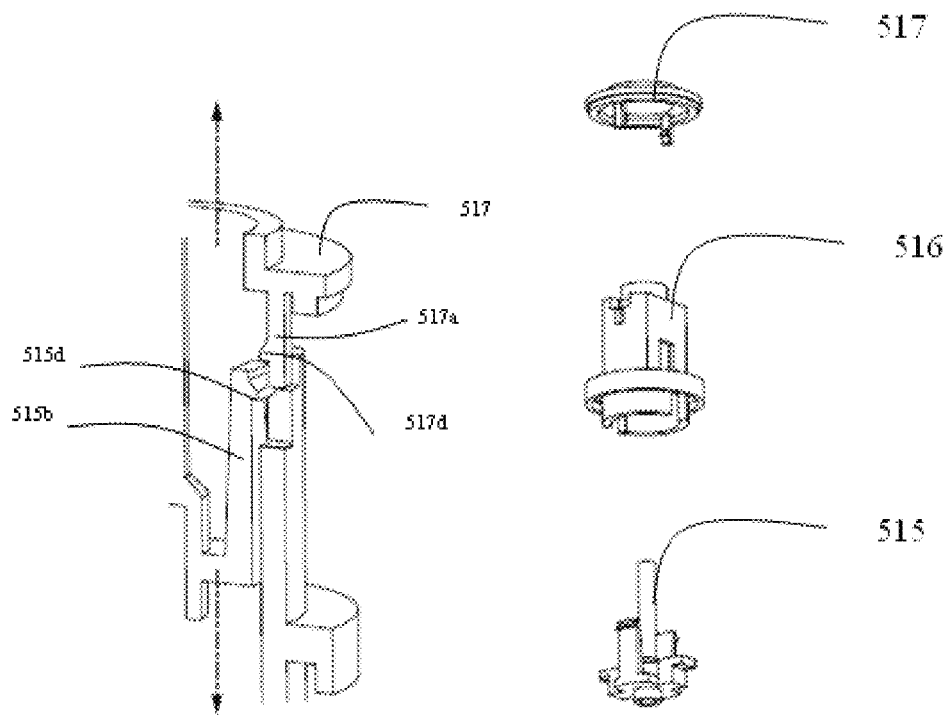

Reference is now made to FIGS. 26a-26d closely illustrating the discharge of the actuator 515 to its initial potion. FIG. 26a illustrates the actuator 515 (namely the bulge 515d) coupled the third complementary actuator 517 (namely to bulge 517d). Once the membrane 508 is elevated (the user takes in air), the third complementary actuator 517 is elevated, thus freeing said bulge 515d of actuator 515 from bulge 517d of the third complementary actuator 517 (see FIG. 26b-26d).

As mentioned above, the main difference between the first embodiment (device 500 illustrated in FIGS. 12-19) and the second embodiment (device 600 illustrated in FIG. 20-26d) is the fact that the device of the first embodiment is reloaded automatically (i.e., once the medicament is released from the intermediate compartment 511, vacuum is created in the same and another dose of medicament is withdrawn to said intermediate compartment 511) and in the seconds embodiment, the loading is manual (i.e., the patient is required to actively load the device 500).

It should be made clear that, simultaneously with the movement of 517 and the return of 515 to its initial position, medicament 506 is released to the patient.

Figure 26E:
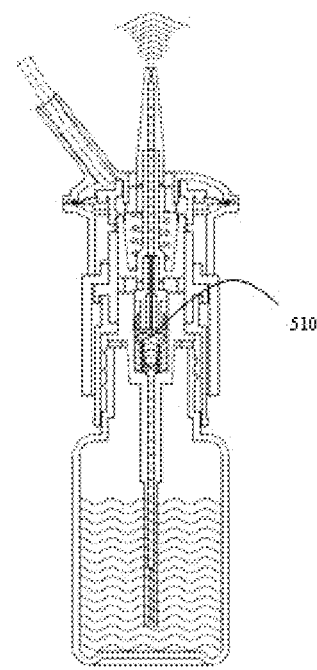

Reference is now made to FIG. 26e which illustrates the same. Once, the membrane 508 is activated, valve 510 is opened and the medicament 506 is released to the nasal cavity.

Figure 27:
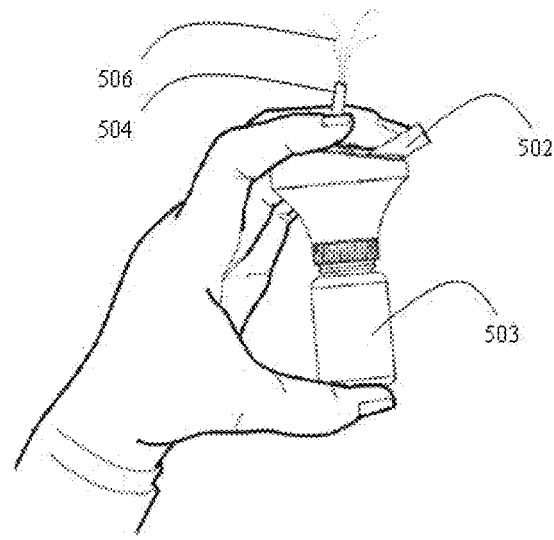
FIGS. 27-28 illustrate another embodiment of the present invention.
Figure 28:
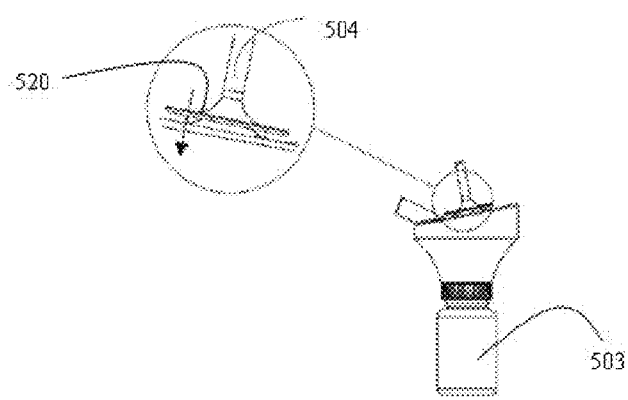

Reference is now made to FIGS. 27-28 illustrating another embodiment of the present invention, in which both the above mentioned mechanisms are actuated not by in taking (inhaling) air by the user. According to FIGS. 27-28, the medicament dispensing is actuated by the pressing (i.e., application of force) on a spring-like surface 520 which is in mechanical communication with membrane 508 and actuates the same.

Such a feature is highly important since, unlike the previous mechanisms (based on the intake of air by the patient, i.e., a subjective feature), this mechanism is based on a press of a button (an objective feature). For example, a relatively ill and weak patient may not have enough strength to inhale the required amount of air so as to activate the mechanism or to take in the required amount of the uni-dose medicament. Such a mechanism eliminates such a problem.

Reference is now made to FIGS. 29-38 illustrating a third mechanism based on the intake of air.

Figures 29, 30:
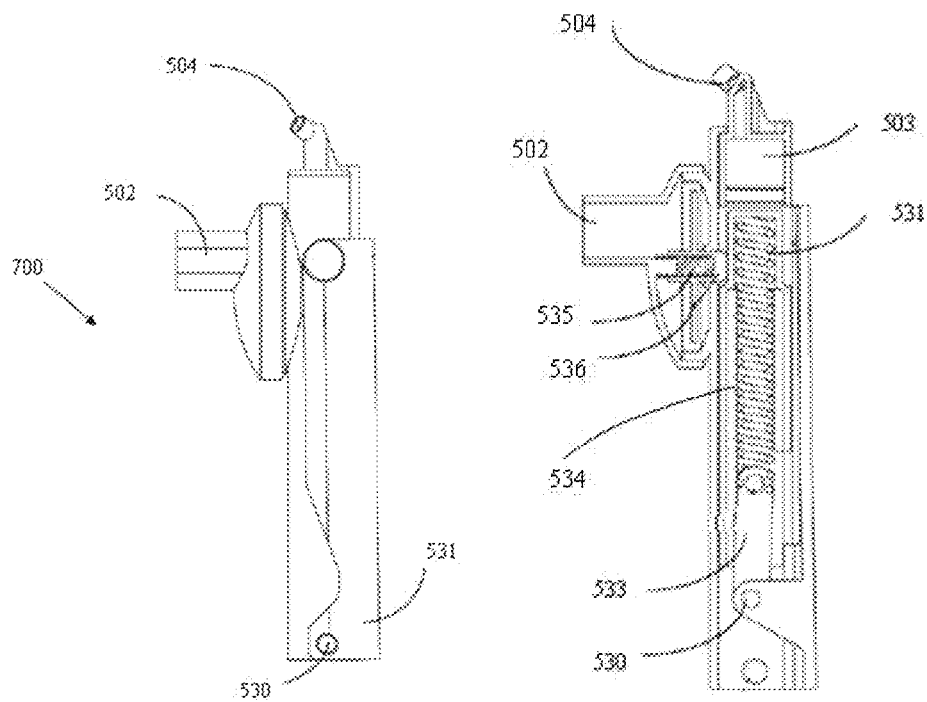

According to the third embodiment the inhaling-actuating device 700 comprises a mouthpiece 502, a nosepiece 504 and an actuator 531 rotated around a hinge 530 (see FIG. 29).

FIG. 30 illustrates a cross sectional view of the same. In the figure, is can be seen that the hinge 530, around which said actuator 531 is rotated, is mechanically coupled to a spring 532 by means of a connector 533. Said spring 532 is maintained retracted (i.e., loaded) by means of a casing 534 (as will be disclosed hereinafter). Said inhaling-actuating device 700 further comprises a container for containing a medicament 506 (not shown).

Reference is now made to FIGS. 31-35, illustrating the actuation of device 700.

Figure 31:
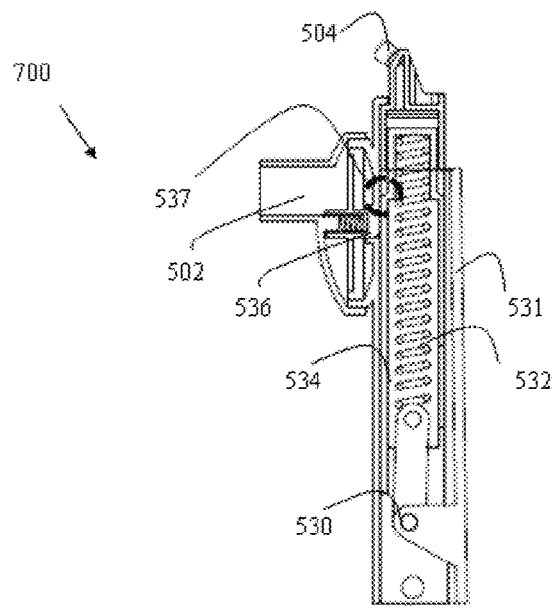
Figure 32:
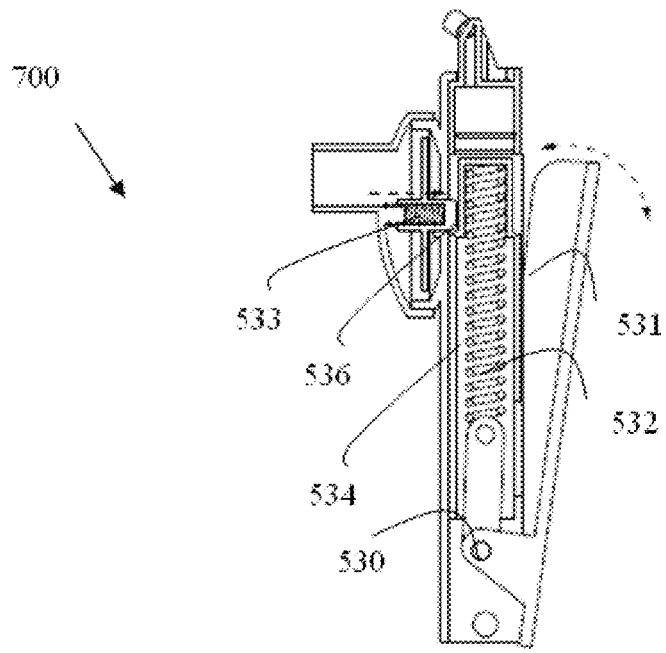

FIG. 31 illustrates device 700 prior to the actuation. FIG. 32 illustrates the first step of the actuation in which actuator 531 is rotated around hinge 530. Said rotation engages spring 532 and loads the same (i.e., compresses the same). A second spring 535, encased within casing 536, is linearly moved along a path which is substantially perpendicular to the main longitudinal axis of spring 532 and casing 534.

Casing 534 of spring 532 is characterized by at least one groove 537 into which at least a portion of casing 536 of spring 535 is inserted so as to maintain spring 532 loaded.

As mentioned, said movement of said spring 535 and casing 536 engages with the casing 534 of spring 532 (namely inserted into groove 537) so as to load (compress) spring 532.

Figures 33, 34:
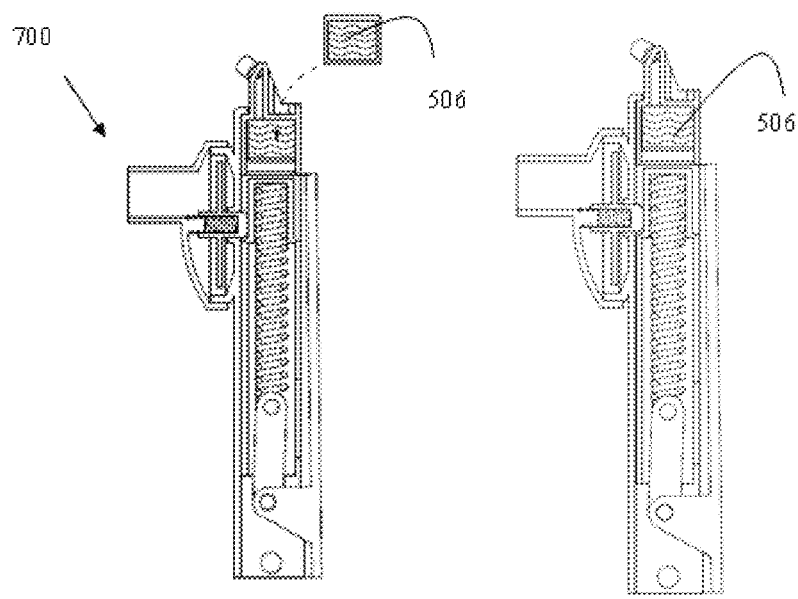

FIGS. 33-34 illustrate the next step, in which medicament 506 is loaded into device 700.

FIG. 35 illustrates the final step in which the device 700 is actuated.

As described above, the activation in initiated by the intake of air by the user. Once the user inhales (see arrows 538) a membrane 508 (which is mechanically coupled to spring 535) is withdrawn from spring 532. Said movement of said membrane withdraws also said spring 535 and casing 536 (from groove 537 of spring 532).

Said withdrawal unloads spring 532 and the same is retracted to the initial position. Said retraction is characterized by a piston-like movement. I.e., when spring 532 is retracted, the same applies compression forces on container 503 so as to be 'pushed' out. Such pushing extracts said medicament 506 and the same is delivered to the nasal cavity of the patient (see arrow 540).

Reference is now made to FIGS. 36-37 which better illustrate the loading stage of the medicament 506 into device 700. Such loading is enabled due to the fact that the top part 550 of device 700 is reversibly coupled to the same.

When spring 502 is loaded (i.e., casing 536 is at least partially within groove 537 of casing 534), the top part 550 of device 700 is de-coupled from device 700 and medicament 506 can be inserted into the same. FIG. 37 illustrates a closer view of the medicament loading.

Reference is now made to FIGS. 38a-38b illustrating the top part 550 prior to and post loading. As seen in FIG. 38a container 503 (containing the medicament 506) is inserted into the complementary top part (sized and shape so as to accommodate the same) 550. FIG. 38b illustrates the top part 550 containing said container 503 containing said medicament 506.

Figures 39, 40:
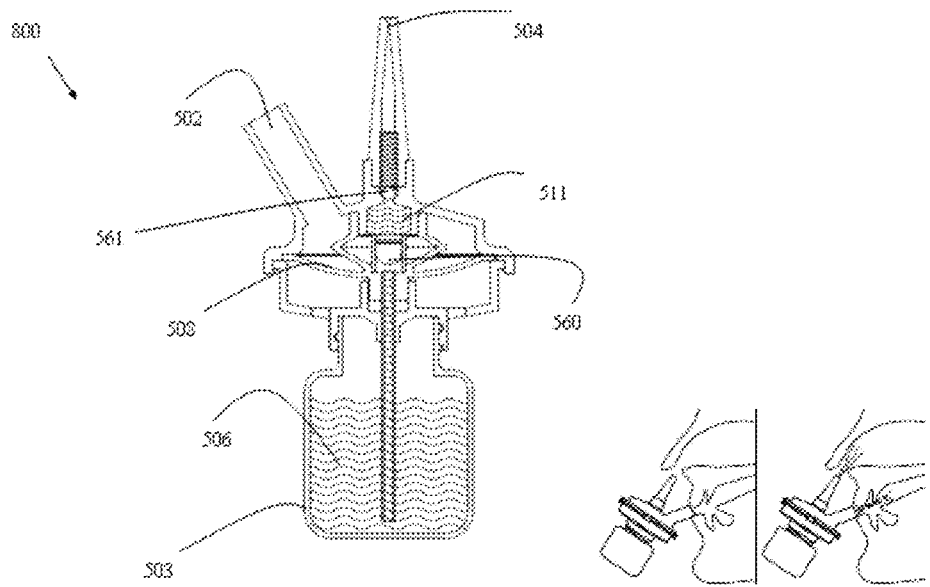
FIGS. 39-41 illustrate a fourth embodiment of the inhaling-actuating device 800.
Figure 41:
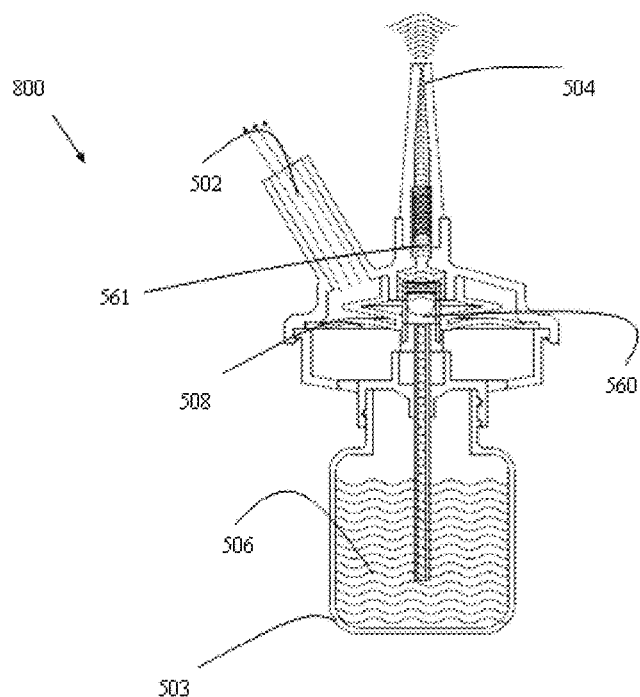

Reference is now made to FIGS. 39-41, illustrating a fourth embodiment of the inhaling-actuating device 800. According to this embodiment, the device 800 comprises a container 503 containing a medicament 506 to be delivered to the nasal cavity, a unidirectional valve 560, an intermediate container 511, a second unidirectional valve 561 and a membrane 508.

Prior to the actuation of the device 800 the intermediate container 511 is filled with a uni-dose amount of medicament 506 (this is enabled due to the fact that once the medicament is released to the nasal cavity, vacuum is generated within the intermediate container 511; thus, medicament is withdrawn into the same through unidirectional valve 561).

Once the patient takes in air (see FIG. 40), device 800 is actuated. Reference is now made to FIG. 40 illustrating the actuation mechanism.

Once the user inhales air (see arrows 562), membrane 508 is elevated. Membrane 508 is mechanically coupled to said valve 560, such that when said membrane 508 is elevated, valve 560 is elevated as well.

The elevation of valve 560 is characterized by a piston-like movement. I.e., when valve 560 is elevated, the same applies pressure on valve 561, such that the medicament 506, contained within intermediate container 511 is now released from the same into the nasal cavity (see arrows 564).

It should be pointed out that it is within the core concept of the present invention in which the nosepiece 504 can be designed and configured to be shaped for either one or two nostrils.

According to some embodiments, the substance can be stored within container 503 under a predetermined pressure. Therefore, when the device 500, 600, 700, 800 is activated, internal pressure within the container 503 delivers or assists in delivery of the substance, so that the substance can be released as aerosol characterized by elevated pressure.

In some embodiments, the device comprises no substance pressurizing mechanism, release of the substance depending on the predetermined pressure only. In some embodiments, such as but not limited to those described herein, release of the substance results from the combined action of the predetermined pressure and the pressurizing or suction mechanism of the device.

In other words, in some embodiments, the stored substance is a pressurized substance stored under pressure.

For non-limiting example, transfer of the uni-dose of substance from container 503 to intermediate container 511 can be by means of the predetermined pressure within the container, while release of the substance from intermediate container 511 can be by means of pressure applied to valve 561.

Any combination of the predetermined pressure of the substance in the container and a pressure or suction developed by a valve or piston can be used to transfer substance from the container to an intermediate container; from a container to the exterior of the device (or the interior of a nostril); from an intermediate container to the exterior of the device (or the interior of a nostril); and any combination thereof.

According to another embodiment of the present invention, the substance stored within container 503 at no pressure and only upon activation of the device (i.e., reconfiguration of the valve from the active configuration to the inactive configuration) the substance is momentarily pressurized and delivered to nose. The substance can be pressurized by means of (a) the spring 532; or, (b) by means of ambient air present in the device and being pressurized by spring 532 and released with the substance upon activation.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An air-intake actuated device configured for delivering a substance to a nasal cavity of a subject, said device comprising:
   a. a container for containing said substance;
   b. a nosepiece extending from said device for placement in proximity to a nose of said subject, said nosepiece being in fluid communication with said container;
   c. a valve mechanically connectable to said container, characterized by at least two configurations: (i) an active configuration in which said valve enables delivery of predetermined amount of said substance from said container to said nasal cavity via said nosepiece; and, (ii) an inactive configuration, in which said valve prevents delivery of said predetermined amount of said substance from said container to said nasal cavity;
   d. a mouthpiece extending from said device for placement in a mouth of said subject; and,
   e. a trigger mechanism configured to reconfigure said valve from said active configuration to said inactive configuration, and vice versa;
   said trigger mechanism is configured to be activated by means of said subject intaking air through said mouthpiece;
   said trigger mechanism is configured to reconfigure said valve from said inactive configuration to said active configuration for a predetermined period of time in response to said subject's intake of air;
   wherein upon activation of said trigger mechanism said substance is momentarily pressurized and delivered from said container to said nasal cavity.

2. The air-intake actuated device according to claim 1, wherein said substance is momentarily pressurized by means of a spring being compressed.

3. The air-intake actuated device according to claim 1, wherein said substance is momentarily pressurized by means of ambient air present in said device being pressurized by spring and delivered with said substance to said nasal cavity.

4. The air-intake actuated device according to claim 1, wherein said substance is storable in said container at a predetermined pressure.

5. The air-intake actuated device according to claim 1, wherein said trigger mechanism is configured to reconfigure said valve from said active configuration to said inactive configuration when said subject ceases said intake of air.

6. The air-intake actuated device according to claim 1, wherein said trigger mechanism comprises a flexible membrane; said membrane is in mechanical communication with said valve; such that said membrane is configured to be relocated from its initial position and said valve is configured to be opened when said subject takes in air.

7. The air-intake actuated device according to claim 1, additionally comprising an intermediate compartment configured to be filled from said container with said predetermined amount of said substance; such that said delivery of said substance is from said intermediate compartment.

8. The air-intake actuated device according to claim 1, wherein the operation of said trigger mechanism is configured to be synchronizable with said intake of air by said subject.

9. The air-intake actuated device according to claim 1, wherein said trigger mechanism comprises a pulsation mechanism configured to reconfigure said valve from said inactive configuration to said active configuration and vice versa in sequence of pulses, each of which is characterized by a predetermined length of pulse, said valve configured to release said predetermined amount of said substance according to said sequence of pulses.

10. The air-intake actuated device according to claim 1, wherein said nosepiece is in fluid communication with said valve by means of a spray nozzle; wherein said spray nozzle is characterized by a diameter which influences said predetermined period of time.

11. The air-intake actuated device according to claim 1, wherein upon reconfiguration of said valve from said inactive configuration to said active configuration pressure is built within said device.

12. The air-intake actuated device according to claim 11, further comprising a cap configured to cover at least a portion of the components of said device for sterilization purposes; wherein said cap comprises an opening.

13. The air-intake actuated device according to claim 12, wherein said cap is breakable upon reach of said pressure to a predetermined pressure.

14. The air-intake actuated device according to claim 1, wherein said container is configured to be connectable to an external container, said external container configured to fill said container with said substance; wherein said external container is configured to fill said container with a predetermined dose of said substance.

15. The air-intake actuated device according to claim 1, further comprising indicating means configured to indicate the amount of said substance within said container; wherein said indicating means is a transparent window located on a side of said container.

16. The air-intake actuated device according to claim 1, wherein said substance is a drug selected from a group consisting of: Anti-Angiogenesis agents, Antisense, anti-ulcer, butorphanol, Calcitonin and analogs, Cyclooxygenase (COX-II) inhibitors, desmopres sin and analogs, dihydroergotamine, Dopamine agonists and antagonists, Enkephalins and other opioid peptides, Growth hormone and analogs, growth hormone releasing hormone, Growth hormone antagonists, Immunoglobulin E (IgE) suppressors, Insulin, insulinotropin and analogs, Ketamine, Kytril (granisetron), Leutenizing hormone releasing hormone and analogs, lidocaine, metoclopramide, Midazolam, Narcotic analgesics, neuraminidase inhibitors, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, vasopressin, and any combination thereof.

17. The air-intake actuated device according to claim 1, wherein said substance is a vaccine with or without carriers and/or adjuvant selected from a group consisting of: Prophylactics and therapeutic antigens, subunit protein, peptide and polysaccharide, polysaccharide conjugates, toxoids, genetic based vaccines, live attenuated reassortant, inactivated whole cells, viral and bacterial vectors for the treatment of arthritis, *Lactobacillus* species: *Lactobacillus acetotolerans, Lactobacillus acidifarinae, Lactobacillus acidipiscis, Lactobacillus acidophilus (Doderlein bacillus), Lactobacillus agilis, Lactobacillus algidus, Lactobacillus alimentarius, Lactobacillus amylolyticus, Lactobacillus amylophilus, Lactobacillus amylotrophicus, Lactobacillus*

*amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustorum, Lactobacillus curvatus, Lactobacillus delbrueckii, Lactobacillus delbrueckii* subsp. *Bulgaricus, Lactobacillus delbrueckii* subsp. *Lactis, Lactobacillus diolivorans, Lactobacillus equi, Lactobacillus equigenerosi, Lactobacillus farraginis, Lactobacillus farciminis, Lactobacillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus hammesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefiranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfrancis censis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae, Lactobacillus zymae*, Probiotics selected from a group consisting of Lactic acid bacteria (LAB) and bifidobacteria, and any combination thereof; said substance is used for the treatment of at least one selected from a group consisting of *cholera, moraxella catarrhali*, cocaine addiction, *Haemophilus influenzae* type b (Hib), meningococcus, measles, mumps, rubella, varicella, yellow fever, Respiratory syncytial virus, pneumococcus, *streptococcus*, typhoid, influenza, hepatitis, including hepatitis A, B, C and F, polio, human immunodeficiency virus (HIV), parainfluenza, rotavirus, cytomegalovirus (CMV), *chlamydia*, non-typeable *haemophilus, moraxella catarrhalis*, human papilloma virus, tuberculosis including *Bacillus* Calmette-Guerin (BCG), gonorrhoea, asthma, atheroschlerosis, malaria, otitis media, *E-coli*, Alzheimer's disease, *H. Pylori, salmonella*, diabetes, cancer, herpes simplex, *Staphylococcus aureus, Streptoccocus*, and any combination thereof.

18. The air-intake actuated device according to claim 1, wherein said substance is used for the treatment of at least one selected from a group consisting of *cholera, moraxella catarrhali*, cocaine addiction, Hib, meningococcus, measles, mumps, rubella, varicella, yellow fever, Respiratory syncytial virus, pneumococcus, *streptococcus*, typhoid, influenza, hepatitis, including hepatitis A, B, C and F, polio, HIV, parainfluenza, rotavirus, CMV, *chlamydia*, non-typeable *haemophilus, moraxella catarrhalis*, human papilloma virus, tuberculosis including BCG, gonorrhoea, asthma, atheroschlerosis, malaria, otitis media, *E-coli, H. Pylori, salmonella*, diabetes, cancer, herpes simplex, *Staphylococcus aureus, Streptoccocus*, central nervous system (CNS) disorders, brain disorders such as: brain cancer, acute brain injury, spinal cord injury, Alzheimer's disease, Neurogenesis, Parkinson's disease, depression, Epilepsy, schizophrenia by the delivery of substances such as: Neurotrophins, brain-derived neurotrophic factor (BDNF), glial cell-derived neurotrophic factor (GDNF), anti-epidermal growth factor receptor antibodies (anti EGF receptor AB), Enzymes such as Lysosomal enzyme, Neuregulin and any combination thereof.

19. The air-intake actuated device according to claim 1, wherein said substance is a therapeutic substance selected from a group consisting of: agents for the common cold, Anti-addiction, anti-infectives, analgesics, anesthetics, anorexics, antiarthritics, anti-allergy agents, antiasthmatic agents, anticonvulsants, anti-depressants, antidiabetic agents, anti-depressants, anti-diuretics, anti-emetics, antihistamines, anti-inflammatory agents, antimigraine preparations, antimotion sickness preparations, antinauseants, antineoplastics, anti-obesity, antiosteoporeteic, antiparkinsonism drugs, antipruritics, antipsychotics, antipyretics, anticholinergics, benzodiazepine antagonists, bone stimulating agents, central nervous system stimulants, hormones, hypnotics, immunosuppressives, prostaglandins, proteins, peptides, polypeptides and other macromolecules, psychostimulants, rhinitis treatment, sedatives, sexual hypofunction, tranquilizers and vitamins including B12, probiotics, natural oils, natural ingredients, a peptide or protein therapeutic agent such as cytokines, hormones, clotting factors, vaccines, monoclonal antibody, natural oils; Mint oils, Peppermint oil, Spearmint oil, Menthol, Olive oil, *Eucalyptus* oil, Amino acids, fatty acids and any combination thereof.

20. The air-intake actuated device according to claim 1, wherein said substance may be delivered to said nasal cavity in a form selected from the group consisting of: a powder; a granule; a cachet; a capsule; a tablet; a paste; a cream; a gel; an ointment, a salve; a foam, a paste; a lotion; a cream; an oil suspension; a spray; a suspension; a solution; an emulsion; a patch; a stick; a spray, preferably a nasal spray, or a buccal spray; a mouth wash; an aerosol from a Venturi effect; and a drink.

21. A method for delivering a substance to a nasal cavity of a subject, said method comprising steps of:
 a. providing an air-intake actuated device configured for delivering a substance to a nasal cavity of a subject, said device comprising: (i) a container for containing said substance; (ii) a nosepiece extending from said device for placement in proximity to a nose of said subject, said nosepiece being in fluid communication with said container; (iii) a valve mechanically connectable to said container, characterized by at least two configurations: (i) an active configuration in which said valve enables delivery of predetermined amount of said substance from said container via said nosepiece to said nasal cavity; and, (ii) an inactive configuration, in which said valve prevents delivery of said predetermined amount of said substance from said container to said nasal cavity; (iv) a mouthpiece extending from said device for placement in a mouth of said subject; and, (v) a trigger mechanism configured to reconfigure said valve from said active configuration to said inactive configuration, and vice versa; wherein said trigger mechanism is activated by means of said subject taking in air through said mouthpiece; further wherein said trigger mechanism is configured to reconfigure said valve from said inactive configuration to said active configuration for a predetermined period of time in response to said subject's intake of air;

b. placing said nosepiece in or around the nose of said subject;

c. placing said mouthpiece in the mouth of said subject; and, d. taking air through said mouthpiece into said mouth of said subject, said intake of air activating said trigger mechanism; thereby: (i) reconfiguring said valve from said inactive configuration to said active configuration for said predetermined period of time; and, (ii) fluidly connecting said container to said nosepiece to enable delivery of said predetermined amount of said substance from said container to said nosepiece wherein upon activation of said trigger mechanism said substance is momentarily pressurized and delivered from said container to said nasal cavity.

22. The method for delivering a substance to a nasal cavity of a subject according to claim 21, wherein said substance is momentarily pressurized by means of a spring being compressed.

23. The method for delivering a substance to a nasal cavity of a subject according to claim 21, wherein said substance is momentarily pressurized by means of ambient air present in said device being pressurized by spring and delivered with said substance to said nasal cavity.

24. The method for delivering a substance to a nasal cavity of a subject according to claim 21, wherein said substance is storable in said container at a predetermined pressure.

25. The method for delivering a substance to a nasal cavity of a subject according to claim 21, further comprising step of reconfiguring said valve via said trigger mechanism from said active configuration to said inactive configuration when said intake of air ceases.

26. The method for delivering a substance to a nasal cavity of a subject according to claim 21, additionally comprising selecting at least one set of steps from a group consisting of (a) providing said trigger mechanism with a flexible membrane, said membrane is in mechanical communication with said valve; intaking air through said mouthpiece, thereby relocating said membrane from its initial position and opening said valve; and (b) providing said device with an intermediate compartment and filling said intermediate compartment from said container with said predetermined amount of said substance; such that said delivery of said substance is from said intermediate compartment.

27. The method for delivering a substance to a nasal cavity of a subject according to claim 21, further comprising step of configuring said trigger mechanism such that operation of said trigger mechanism is synchronizable with said intake of air by said subject.

28. The method for delivering a substance to a nasal cavity of a subject according to claim 21, further comprising a step of providing said trigger mechanism with a pulsation mechanism configured to reconfigure said valve from said inactive configuration to said active configuration and vice versa in sequence of pulses, each of which is characterized by a predetermined length of pulse, said valve configured to deliver said predetermined amount of said substance according to said sequence of pulses; further comprising a step of delivering in each said pulse at least two doses of said predetermined amount of said substance.

29. The method for delivering a substance to a nasal cavity of a subject according to claim 21, wherein said nosepiece is in fluid communication with said valve by means of a spray nozzle; further wherein said spray nozzle is characterized by a diameter which influences said predetermined period of time.

30. The method for delivering a substance to a nasal cavity of a subject according to claim 21, wherein upon reconfiguration of said valve from said inactive configuration to said active configuration pressure is built within said device.

31. The method for delivering a substance to a nasal cavity of a subject according to claim 30, further comprising step of providing said device with a cap configured to cover at least a portion of the components of said device for sterilization purposes; wherein said cap comprises an opening.

32. The method for delivering a substance to a nasal cavity of a subject according to claim 31, wherein said cap is breakable upon reach of said pressure to a predetermined pressure.

33. The method for delivering a substance to a nasal cavity of a subject according to claim 21, additionally comprising steps of connecting said container to an external container, and filling said container by said external container with a predetermined dose of said substance.

34. The method for delivering a substance to a nasal cavity of a subject according to claim 21, additionally comprising steps of providing said container with indicating means configured to indicate the amount of said substance within said container; and providing said indicating means as a transparent window located on a side of said container.

35. The method for delivering a substance to a nasal cavity of a subject according to claim 21, additionally comprising steps of selecting said substance to be a drug and selecting said drug from a group consisting of: Anti-Angiogenesis agents, Antisense, anti-ulcer, butorphanol, Calcitonin and analogs, COX-II inhibitors, desmopressin and analogs, dihydroergotamine, Dopamine agonists and antagonists, Enkephalins and other opioid peptides, Growth hormone and analogs, growth hormone releasing hormone, Growth hormone antagonists, IgE suppressors, Insulin, insulinotropin and analogs, Ketamine, Kytril, Leutenizing hormone releasing hormone and analogs, lidocaine, metoclopramide, Midazolam, Narcotic analgesics, neuraminidase inhibitors, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, vasopressin, and any combination thereof.

36. The method for delivering a substance to a nasal cavity of a subject according to claim 21, additionally comprising steps of selecting said substance from a vaccine with or without carriers or adjuvant and selecting said vaccine from a group consisting of: Prophylactics and therapeutic antigens, subunit protein, peptide and polysaccharide, polysaccharide conjugates, toxoids, genetic based vaccines, live attenuated reassortant, inactivated whole cells, viral and bacterial vectors for the treatment of arthritis, *Lactobacillus* species: *Lactobacillus acetotolerans, Lacto-* bacillus acidifarinae, Lactobacillus acidipiscis, Lactobacillus acidophilus (Doderlein bacillus), Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustorum, Lactobacillus curvatus, Lactobacillus delbrueckii, Lactobacillus delbrueckii subsp. Bulgaricus, Lactobacillus delbrueckii subsp. Lactis, Lactobacillus dioliovorans, Lactobacillus equi, Lactobacillus equigenerosi, Lactobacillus farraginis, Lactobacillus farciminis, Lactobacillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus hammesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefiranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae, Lactobacillus zymae, Probiotics selected from a group consisting of Lactic acid bacteria (LAB) and bifidobacteria, and any combination thereof; said substance is used for the treatment of at least one selected from a group consisting of cholera, moraxella catarrhalis, cocaine addiction, Hib, meningococcus, measles, mumps, rubella, varicella, yellow fever, Respiratory syncytial virus, pneumococcus, *streptococcus*, typhoid, influenza, hepatitis, including hepatitis A, B, C and F, polio, HIV, parainfluenza, rotavirus, CMV, *chlamydia*, non-typeable *haemophilus*, *moraxella catarrhalis*, human papilloma virus, tuberculosis including BCG, gonorrhoea, asthma, atherosclerosis, malaria, otitis media, *E-coli*, Alzheimer's disease, *H. Pylori*, *salmonella*, diabetes, cancer, herpes simplex, *Staphylococcus aureus*, Streptoccocus, and any combination thereof.

37. The method for delivering a substance to a nasal cavity of a subject according to claim 21, additionally comprising a step of selecting said substance for treatment of at least one selected from a group consisting of cholera, *moraxella* catarrhali, cocaine addiction, Hib, meningococcus, measles, mumps, rubella, varicella, yellow fever, Respiratory syncytial virus, pneumococcus, *streptococcus*, typhoid, influenza, hepatitis, including hepatitis A, B, C and F, polio, HIV, parainfluenza, rotavirus, CMV, *chlamydia*, non-typeable *haemophilus, moraxella catarrhalis*, human papilloma virus, tuberculosis including BCG, gonorrhoea, asthma, atherosclerosis, malaria, otitis media, *E-coli, H. Pylori, salmonella*, diabetes, cancer, herpes simplex, *Staphylococcus aureus*, Streptoccocus, CNS disorders, brain disorders such as: brain cancer, acute brain injury, spinal cord injury, Alzheimer's disease, Neurogenesis, Parkinson's disease, depression, Epilepsy, schizophrenia by the delivery of substances such as: Neurotrophins, BDNF, GDNF, anti EGF receptor AB, Enzymes such as Lysosomal enzyme, Neuregulin and any combination thereof.

38. The method for delivering a substance to a nasal cavity of a subject according to claim 21, additionally comprising steps of selecting said substance to be a therapeutic substance and selecting said therapeutic substance from a group consisting of: Agents for the common cold, Anti-addiction, anti-infectives, analgesics, anesthetics, anorexics, antiarthritics, anti-allergy agents, antiasthmatic agents, anticonvulsants, anti-depressants, antidiabetic agents, anti-depressants, anti-diuretics, anti-emetics, antihistamines, anti-inflammatory agents, antimigraine preparations, antimotion sickness preparations, antinauseants, antineoplastics, anti-obesity, antiosteoporeteic, antiparkinsonism drugs, antipruritics, antipsychotics, antipyretics, anticholinergics, benzodiazepine antagonists, bone stimulating agents, central nervous system stimulants, hormones, hypnotics, immunosuppressives, prostaglandins, proteins, peptides, polypeptides and other macromolecules, psychostimulants, rhinitis treatment, sedatives, sexual hypofunction, tranquilizers and vitamins including B12, probiotics, natural oils, natural ingredients, peptide or protein therapeutic agent such as cytokines, hormones, clotting factors, vaccines, monoclonal antibody, natural oils; Mint oils, Peppermint oil, Spearmint oil, Menthol, Olive oil, *Eucalyptus* oil, Amino acids, fatty acids and any combination thereof.

39. The method for delivering a substance to a nasal cavity of a subject according to claim 21, additionally comprising a step of delivering said substance to said nasal cavity in a form selected from a group consisting of: a powder; a granule; a cachet; a capsule; a tablet; a paste; a cream; a gel; an ointment; a salve; a foam; a paste; a lotion; a cream; an oil suspension; a spray; a suspension; a solution; an emulsion; a patch; a stick; a spray, preferably a nasal spray, or a buccal spray; a mouth wash; an aerosol from a Venturi effect, and a drink.

* * * * *